United States Patent
Adamo et al.

(10) Patent No.: US 12,409,231 B2
(45) Date of Patent: Sep. 9, 2025

(54) CYCLOALKYNE DERIVATIZED SACCHARIDES

(71) Applicant: GLAXOSMITHKLINE BIOLOGICALS SA, Rixensart (BE)

(72) Inventors: Roberto Adamo, Siena (IT); Francesco Berti, Siena (IT); Qi-Ying Hu, Cambridge, MA (US)

(73) Assignee: GlaxosmithKline Biologicals SA, Rixensart (BE)

( * ) Notice: Subject to any disclaimer, the term of this patent is extended or adjusted under 35 U.S.C. 154(b) by 406 days.

(21) Appl. No.: 17/320,482

(22) Filed: May 14, 2021

(65) Prior Publication Data

US 2021/0268116 A1    Sep. 2, 2021

Related U.S. Application Data

(62) Division of application No. 14/760,916, filed as application No. PCT/EP2014/050483 on Jan. 13, 2014, now Pat. No. 11,135,300.

(30) Foreign Application Priority Data

Jan. 15, 2013 (GB) .................................... 1300707

(51) Int. Cl.
| | | |
|---|---|---|
| A61K 47/55 | (2017.01) | |
| A61K 39/09 | (2006.01) | |
| A61K 47/54 | (2017.01) | |
| A61K 47/64 | (2017.01) | |
| C08B 37/00 | (2006.01) | |

(52) U.S. Cl.
CPC ............ *A61K 47/55* (2017.08); *A61K 39/092* (2013.01); *A61K 47/54* (2017.08); *A61K 47/646* (2017.08); *C08B 37/006* (2013.01)

(58) Field of Classification Search
CPC ...... A61K 47/54; A61K 47/55; A61K 47/646; A61K 39/092
See application file for complete search history.

(56) References Cited

U.S. PATENT DOCUMENTS

2012/0208722 A1    8/2012    Dluhy et al.

FOREIGN PATENT DOCUMENTS

| WO | 03080678 A1 | 10/2003 |
|---|---|---|
| WO | 2006050341 A2 | 5/2006 |
| WO | 2006082530 A2 | 8/2006 |
| WO | 2009067663 A1 | 5/2009 |
| WO | 2011079315 A1 | 6/2011 |
| WO | 2011136645 A1 | 11/2011 |
| WO | 2012035519 A1 | 3/2012 |
| WO | 2012047663 A2 | 4/2012 |
| WO | 2012177701 A2 | 12/2012 |
| WO | WO2013078562 A2 * | 6/2013 |

OTHER PUBLICATIONS

Gierlich, J. et al., Organic Letters, "Click Chemistry as a Reliable Method for the High-Density Postsynthetic Functionalization of Alkyne-Modified DNA", 2006, vol. 8, No. 17, pp. 3639-3642 (Year: 2006).*
MacKenzie, Douglas A. et al., Current Opinion in Chemical Biology, "Strain-promoted cycloadditions involving nitrones and alkynes-rapid tunable reactions for bioorthogonal labeling", 2014, vol. 21, pp. 81-88 (Year: 2014).*
Beal, D. M. et al., Organic & Biomolecular Chemistry, "Click-enabled heterotrifunctional template for sequential bioconjugates", 2012, vol. 10, p. 548-554.
Boons, G-J., Carbohydrate Chemistry, "Bioorthogonal chemical reporter methodology for visualization, isolation and analysis of glycoconjugates," 2010, vol. 36, pp. 152-167.
Borrmann et al., "Genetic Encoding of a Bicyclo[6.1.0]nonyne? Charged Amino Acid Enables Fast Cellular Protein Imaging by Metal?Free Ligation," ChemBioChem, 2012, vol. 13, pp. 2094-2099.
Codelli, J. A. et al., JAGS, "Second-Generation Difluorinated Cylooctynes for Copper-Free Click Chemistry", 2008, vol. 130, pp. 11486-11493.
Constantino, P. et al., Expert Opinion on Drug Discovery, "The design of semi-synthetic and synthetic glycoconjugate vaccines," 2011, vol. 6, No. 10, pp. 1045-1066.
"Derivative", Merriam-Webster Online Dictionary, available at http://www.merriam-webster.com/dictionary/derivative; <http://www.merriam-webster.com/dictionary/derivative%3B>last accessed Jul. 15, 2009.
Droumaguet & Velonia, "Click Chemistry: A Powerful Tool to Creat Polymer-Based Macromolecular Chimeras," Macromolecular Rapid Communications, 2008, vol. 29 pp. 1073-1089.
Hotha & Kashyap, "Click Chemistry" Inspired Synthesis of pseudo-Oligosaccharides and Amino Acid Glycoconjugates, The Journal of Organic Chemistry, 2006, vol. 71, pp. 364-367.
International Search Report for PCT/EP2014/050483, mailed Mar. 21, 2014.
Lallana et al., "Surpassing the Use of Copper in the Click Functionalization of Polymeric Nanostructures: A Strain-Promoted Approach," Journal of the American Chemical Society, 2009, vol. 131, pp. 5748-5750.
Schultz, M. K. et al., Organic Letters, "Synthesis of a DOTA-Biotin Conjugate for Radionuclide Chelation via Cu-Free Click Chemistry", 2010, vol. 12, No. 10, pp. 2398-2401 (Year: 2010).
Sharma et al., "Enzyme-Linked Small-Molecule Detection Using Split Aptamer Ligation," Analytical Chemistry, 2012, vol. 84, pp. 6104-6109.

(Continued)

*Primary Examiner* — Bahar Craigo

(57) ABSTRACT

This disclosure provides novel saccharide derivatives, conjugates, and methods for making the derivatives and conjugates.

13 Claims, 12 Drawing Sheets

(56) References Cited

OTHER PUBLICATIONS

Wan et al., "A Potentially Valuable Advance in the Synthesis of Carbohydrate-Based Anticancer Vaccines through Extended Cycloaddition Chemistry," The Journal of Organic Chemistry, 2006, vol. 71, pp. 8244-8249.
International Preliminary Report on Patentability for International Application No. PCT/EP2014/050483, mailed Jul. 30, 2015, 10 Pages.

* cited by examiner

CYCLOALKYNE DERIVATIZED SACCHARIDES

TECHNICAL FIELD

This invention is in the field of saccharide derivatives, conjugates including saccharides and methods for producing the saccharide derivatives and conjugates. The conjugates are useful for immunisation.

BACKGROUND OF THE INVENTION

The capsular saccharides of bacteria have been used for many years in vaccines against capsulated bacteria. As saccharides are T-independent antigens, however, they are poorly immunogenic. Conjugation to a carrier can convert T-independent antigens into T-dependent antigens, thereby enhancing memory responses and allowing protective immunity to develop.

While classical procedures for conjugation (reductive amination, amide bond formation, etc.) rely on the random reaction of the polysaccharide to the amines of the carrier protein, novel conjugation methods enabling site specific installation of a ligand onto a protein are emerging [1]. Site specific conjugation, besides providing more homogeneous biomolecules as vaccine candidates, could aid to preserve the immunogenicity of the protein.

The click chemistry approach has been described as a method for the formation of complex substances by joining small subunits together in a modular fashion [2, 3]. Various forms of click chemistry reaction are known in the art, such as the Huisgen 1,3-dipolar cycloaddition copper catalyzed reaction [4], which is often referred to as the "click reaction". Other alternatives include cycloaddition reactions such as the Diels-Alder, nucleophilic substitution reactions (especially to small strained rings like epoxy and aziridine compounds), carbonyl chemistry formation of urea compounds and reactions involving carbon-carbon double bonds, such as alkynes in thiol-yne reactions.

The azide-alkyne Huisgen cycloaddition reaction uses a copper catalyst in the presence of a reducing agent to catalyze the reaction of a terminal alkyne group attached to a first molecule. In the presence of a second molecule comprising an azide moiety, the azide reacts with the activated alkyne to form a 1,4-di-substituted 1,2,3-triazole. The copper catalyzed reaction occurs at room temperature and is sufficiently specific that purification of the reaction product is often not required [5]. The azide and alkyne functional groups are largely inert towards biomolecules in aqueous medium, allowing the reaction to occur in complex solutions. The triazole formed is chemically stable and is not subject to enzymatic cleavage, making the click chemistry product highly stable in biological systems. However, the copper catalyst is toxic to living cells, precluding biological applications.

A copper-free click reaction has been proposed [6], which uses ring strain (in a cyclooctyne ring) in place of the copper catalyst to promote a [3+2] azide-alkyne cycloaddition reaction. The closed ring structure induces a substantial bond angle deformation of the acetylene, which is highly reactive with azide groups to form a triazole.

It is an object of the present invention to provide further and improved methods for derivatizing saccharides. It is another object of the present invention to provide further and improved methods for conjugating saccharides to various moieties, such as carrier proteins. Is is also an objection of the invention to provide a conjugation method which yields conjugates with more uniform structures. It is also an object of the invention to provide conjugates with improved immunogenic properties.

SUMMARY OF THE INVENTION

The inventors have developed new processes for derivatizing saccharides and for conjugation of such saccharide derivatives to other moieties. The inventors have also produced novel saccharide derivatives and conjugates which have improved properties over saccharide derivatives and conjugates known in the art. In particular, the conjugates of the invention may have improved immunological properties.

In one aspect, the invention provides a method of derivatizing a saccharide comprising attaching an eight-membered cycloalkyne group to the saccharide. The invention also provides a saccharide derivative comprising an eight-membered cycloalkyne group. The saccharide derivative comprising an eight-membered cycloalkyne group may be obtained or obtainable by the method of derivatizing a saccharide.

In another aspect, the invention provides a method of conjugating a saccharide derivative to an azide-containing moiety, comprising reacting the eight-membered cycloalkyne group with the azide to form a triazole linkage. The invention also provides a conjugate of a saccharide derivative and an azide-containing moiety, wherein the conjugate has the formula R-S-T, wherein R comprises a residue of the saccharide derivative, S is a triazole group fused to an eight-membered cycloalkyl group and T comprises a residue of the moiety azide-containing moiety.

The conjugate may be obtained or obtainable by the method of conjugating a saccharide derivative to an azide-containing moiety of the invention.

The present invention also relates to pharmaceutical compositions comprising a conjugate of the invention in combination with a pharmaceutically acceptable carrier.

The present invention further relates to methods for raising an immune response in a mammal, comprising administering a conjugate or pharmaceutical composition of the invention to the mammal.

DETAILED DESCRIPTION OF THE INVENTION

Figure 1:
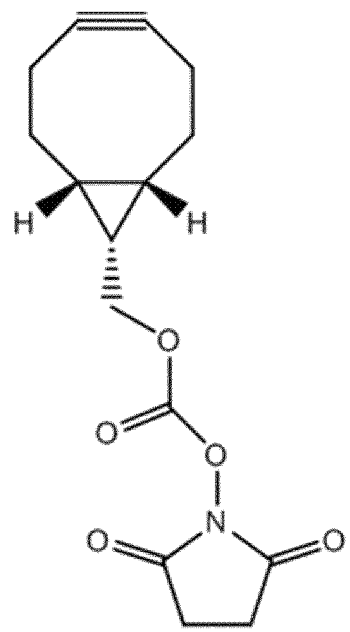
FIG. 1 shows three cyclooctyne-containing compounds.
Figure 1:
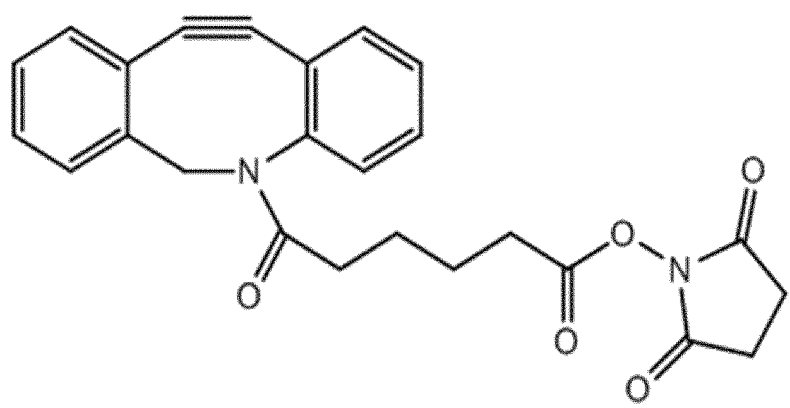
Figure 1:
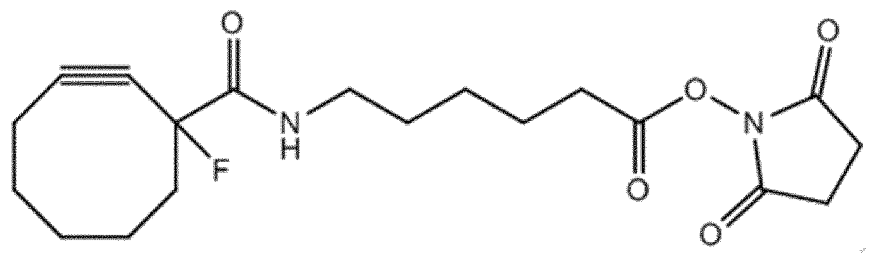

The invention involves methods of derivatizing a saccharide and methods of conjugating a saccharide derivative to an azide-containing moiety. The invention also involves novel saccharide derivatives and conjugates. The features of these methods, saccharide derivatives and conjugates are described in detail below.

Method of Derivatizing a Saccharide

The invention is based on novel saccharide derivatives and methods of producing such saccharide derivatives.

The Saccharide

The saccharide used in the methods of the invention may be any saccharide, particularly a saccharide from a pathogenic organism. Exemplary saccharides for use in the methods of the invention are described below. In particular, the saccharide may be a bacterial saccharide, e.g. a bacterial capsular saccharide.

The saccharides may be used in the form of oligosaccharides. These are conveniently formed by fragmentation of purified polysaccharide (e.g. by hydrolysis), which will usually be followed by purification of the fragments of the desired size. Saccharides may be purified from natural sources. As an alternative to purification, saccharides may be obtained by total or partial synthesis.

S. agalactiae Capsular Saccharides

Preferred bacterial capsular saccharides include those from *Streptococcus agalactiae* ("GBS"). The capsular saccharide is covalently linked to the peptidoglycan backbone of GBS, and is distinct from the group B antigen, which is another saccharide that is attached to the peptidoglycan backbone.

GBS is a leading cause of severe bacterial infections in early 3 months of life among newborns and of septic morbidity among mothers [7]. GBS is also an important cause of morbidity and mortality among non-pregnant adults, particularly among old people and adults with underlying medical conditions. All GBS strains possess a capsular polysaccharide (CPS) on their surface, which is a major virulence factor. Ten different CPS serotypes have been characterized (Ia, Ib, II, III, IV, V, VI, VII, VIII and IX), of which five (Ia, Ib, II, III, V) are responsible for the majority of the neonatal disease in North America and Europe. Monovalent conjugate vaccines have been prepared against serotypes Ia, Ib, II, III, IV, V, VI, VII, VIII and effectiveness demonstrated in animal models3. Recently, it has been demonstrated that GBS pilus proteins, besides being important structures in bacterial adhesion and invasion, seem to be more conserved than those of other Gram-positive bacteria [8].

The GBS capsular saccharides are chemically related, but are antigenically very different. All GBS capsular saccharides share the following trisaccharide core:

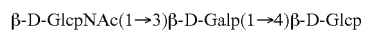

β-D-GlcpNAc(1→3)β-D-Galp(1→4)β-D-Glcp

The various GBS serotypes differ by the way in which this core is modified. GBS-related disease arises primarily from serotypes Ia, Ib, II, III, IV, V, VI, VII, and VIII, with over 85% being caused by five serotypes: Ia, Ib, III & V. The invention may use a saccharide from any serotype, in particular serotypes Ia, Ib, II, III & V.

Saccharides used in the methods of the invention may be in their native form, or may have been modified. For example, the saccharide may be shorter than the native capsular saccharide, or may be chemically modified. In particular, the serotype V capsular saccharide used in the invention may be modified as described in refs. 9 and 10. For example, a serotype V capsular saccharide that has been substantially desialylated. Desialylated GBS serotype V capsular saccharide may be prepared by treating purified GBS serotype V capsular saccharide under mildly acidic conditions (e.g. 0.1M sulphuric acid at 80° C. for 60 minutes) or by treatment with neuraminidase, as described in reference 9. The saccharide used according to the invention may be a substantially full-length capsular polysaccharide, as found in nature, or it may be shorter than the natural length. Full-length polysaccharides may be depolymerised to give shorter fragments for use with the invention e.g. by hydrolysis in mild acid, by heating, by sizing chromatography, etc. In particular, the serotype II and/or III capsular saccharides used in the invention may be depolymerised as described in refs. 11 and 12.

The saccharide may be chemically modified relative to the capsular saccharide as found in nature. For example, the saccharide may be de-O-acetylated (partially or fully), de-N-acetylated (partially or fully), N-propionated (partially or fully), etc. De-acetylation may occur before, during or after conjugation, but preferably occurs before conjugation. Depending on the particular saccharide, de-acetylation may or may not affect immunogenicity. The relevance of O-acetylation on GBS saccharides in various serotypes is discussed in reference 13, and in some embodiments O-acetylation of sialic acid residues at positions 7, 8 and/or 9 is retained before, during and after conjugation e.g. by protection/de-protection, by re-acetylation, etc. However, typically the GBS saccharide used in the present invention has substantially no O-acetylation of sialic acid residues at positions 7, 8 and/or 9. In particular, when the GBS saccharide has been purified by base extraction as described below, then O-acetylation is typically lost. The effect of de-acetylation etc. can be assessed by routine assays.

Capsular saccharides can be purified by known techniques, as described in 14. A typical process involves base extraction, centrifugation, filtration, RNase/DNase treatment, protease treatment, concentration, size exclusion chromatography, ultrafiltration, anion exchange chromatography, and further ultrafiltration. Treatment of GBS cells with the enzyme mutanolysin, which cleaves the bacterial cell wall to free the cell wall components, is also useful.

As an alternative, the purification process described in reference 15 can be used. This involves base extraction, ethanol/CaCl$_2$) treatment, CTAB precipitation, and re-solubilisation. A further alternative process is described in reference 16.

N. Meningitidis Capsular Saccharides

The saccharide may be a bacterial capsular saccharide. Exemplary bacterial capsular saccharides include those from N. meningitidis. Based on the organism's capsular polysaccharide, various serogroups of N. meningitidis have been identified, including A, B, C, H, I, K, L, 29E, W135, X, Y & Z. The saccharide in the invention may be from any of these serogroups. Typically, the saccharide is from one of the following meningococcal serogroups: A, C, W135 and Y.

The capsular saccharides will generally be used in the form of oligosaccharides. These are conveniently formed by fragmentation of purified capsular polysaccharide (e.g. by hydrolysis), which will usually be followed by purification of the fragments of the desired size.

Fragmentation of polysaccharides is typically performed to give a final average degree of polymerisation (DP) in the oligosaccharide of less than 30 (e.g. between 10 and 20, preferably around 10 for serogroup A; between 15 and 25 for serogroups W135 and Y, preferably around 15-20; between 12 and 22 for serogroup C; etc.). DP can conveniently be measured by ion exchange chromatography or by colorimetric assays [17].

If hydrolysis is performed, the hydrolysate will generally be sized in order to remove short-length oligosaccharides [18]. This can be achieved in various ways, such as ultrafiltration followed by ion-exchange chromatography. Oligosaccharides with a degree of polymerisation of less than or equal to about 6 are preferably removed for serogroup A, and those less than around 4 are preferably removed for serogroups W135 and Y.

Chemical hydrolysis of saccharides generally involves treatment with either acid or base under conditions that are standard in the art. Conditions for depolymerisation of capsular saccharides to their constituent monosaccharides are known in the art. One depolymerisation method involves the use of hydrogen peroxide [19]. Hydrogen peroxide is added to a saccharide (e.g. to give a final $H_2O_2$ concentration of 1%), and the mixture is then incubated (e.g. at around 55° C.) until a desired chain length reduction has been achieved. The reduction over time can be followed by removing samples from the mixture and then measuring the (average) molecular size of saccharide in the sample. Depolymerization can then be stopped by rapid cooling once a desired chain length has been reached Serogroups C, W135 and Y Techniques for preparing capsular polysaccharides from meningococci have been known for many years, and typically involve a process comprising the steps of polysaccharide precipitation (e.g. using a cationic detergent), ethanol fractionation, cold phenol extraction (to remove protein) and ultracentrifugation (to remove LPS) [e.g. see ref. 20].

A more preferred process involves polysaccharide precipitation followed by solubilisation of the precipitated polysaccharide using a lower alcohol. Precipitation can be achieved using a cationic detergent such as tetrabutylammonium and cetyltrimethylammonium salts (e.g. the bromide salts), or hexadimethrine bromide and myristyltrimethylammonium salts. Cetyltrimethylammonium bromide ('CTAB') is particularly preferred [22]. Solubilisation of the precipitated material can be achieved using a lower alcohol such as methanol, propan-1-ol, propan-2-ol, butan-1-ol, butan-2-ol, 2-methyl-propan-1-ol, 2-methyl-propan-2-ol, diols, etc., but ethanol is particularly suitable for solubilising CTAB-polysaccharide complexes. Ethanol may be added to the precipitated polysaccharide to give a final ethanol concentration (based on total content of ethanol and water) of between 50% and 95%.

After re-solubilisation, the polysaccharide may be further treated to remove contaminants. This is particularly important in situations where even minor contamination is not acceptable (e.g. for human vaccine production). This will typically involve one or more steps of filtration e.g. depth filtration, filtration through activated carbon may be used, size filtration and/or ultrafiltration.

Once filtered to remove contaminants, the polysaccharide may be precipitated for further treatment and/or processing. This can be conveniently achieved by exchanging cations (e.g. by the addition of calcium or sodium salts).

Further and alternative methods for purification of meningococcal saccharides are disclosed in references 19 & 23.

As an alternative to purification, capsular saccharides of the present invention may be obtained by total or partial synthesis e.g. Hib synthesis is disclosed in ref. 24, and MenA synthesis in ref. 25.

The saccharide may be chemically modified e.g. it may be O-acetylated or de-O-acetylated. Any such de-O-acetylation or hyper-acetylation may be at specific positions in the saccharide. For instance, most serogroup C strains have O-acetyl groups at position C-7 and/or C-8 of the sialic acid residues, but about 15% of clinical isolates lack these O-acetyl groups [26,27]. The acetylation does not seem to affect protective efficacy (e.g. unlike the Menjugate™ product, the Neis Vac-C™ product uses a de-O-acetylated saccharide, but both vaccines are effective). The serogroup W135 saccharide is a polymer of sialic acid-galactose disaccharide units. The serogroup Y saccharide is similar to the serogroup W135 saccharide, except that the disaccharide repeating unit includes glucose instead of galactose. Like the serogroup C saccharides, the MenW135 and MenY saccharides have variable O-acetylation, but at sialic acid 7 and 9 positions [28].

Serogroup A

The method may include a serogroup A capsular saccharide antigen. The saccharide can be purified and conjugated in the same way as for serogroups C, W135 and Y (see above), although it is structurally different—whereas the capsules of serogroups C, W135 and Y are based around sialic acid (N-acetyl-neuraminic acid, NeuAc), the capsule of serogroup A is based on N-acetyl-mannosamine, which is the natural precursor of sialic acid. The serogroup A saccharide is particularly susceptible to hydrolysis, and its instability in aqueous media means that (a) the immunogenicity of liquid vaccines against serogroup A declines over time, and (b) quality control is more difficult, due to release of saccharide hydrolysis products into the vaccine.

Native MenA capsular saccharide is a homopolymer of ($\alpha$1→6)-linked N-acetyl-D-mannosamine-1-phosphate, with partial O-acetylation at C3 and C4. The principal glycosidic bond is a 1-6 phosphodiester bond involving the hemiacetal group of C1 and the alcohol group of C6 of the D-mannosamine. The average chain length is 93 monomers. It has the following formula:

A modified saccharide antigen has been prepared which retains the immunogenic activity of the native serogroup A saccharide but which is much more stable in water. Hydroxyl groups attached at carbons 3 and 4 of the monosaccharide units are replaced by a blocking group [refs. 29 and 30].

The number of monosaccharide units having blocking groups in place of hydroxyls can vary. For example, all or substantially all the monosaccharide units may have blocking groups. Alternatively, at least 10%, 20%, 30%, 40%, 50%, 60%, 70%, 80% or 90% of the monosaccharide units may have blocking groups. At least 1, 2, 3, 4, 5, 6, 7, 8, 9, 10, 11, 12, 13, 14, 15, 16, 17, 18, 19, 20, 21, 22, 23, 24, 25, 26, 27, 28, 29 or 30 monosaccharide units may have blocking groups.

Likewise, the number of blocking groups on a monosaccharide unit may vary. For example, the number of blocking groups on any particular monosaccharide unit may be 1 or 2.

Blocking groups to replace hydroxyl groups may be directly accessible via a derivatizing reaction of the hydroxyl group i.e. by replacing the hydrogen atom of the hydroxyl group with another group. Suitable derivatives of hydroxyl groups which act as blocking groups are, for example, carbamates, sulfonates, carbonates, esters, ethers (e.g. silyl ethers or alkyl ethers) and acetals. Some specific examples of such blocking groups are allyl, Aloc, benzyl, BOM, t-butyl, trityl, TBS, TBDPS, TES, TMS, TIPS, PMB, MEM, MOM, MTM, THP, etc. Other blocking groups that are not directly accessible and which completely replace the hydroxyl group include $C_{1-12}$ alkyl, $C_{3-12}$ alkyl, $C_{5-12}$ aryl, $C_{5-12}$ aryl-$C_{1-6}$ alkyl, $NR^1R^2$ ($R^1$ and $R^2$ are defined in the following paragraph), H, F, Cl, Br, $CO_2H$, $CO_2(C_{1-6}$ alkyl), CN, $CF_3$, $CCl_3$, etc.

Typical blocking groups are of the formula: —O—X—Y or —$OR^3$ wherein: X is C(O), S(O) or $SO_2$; Y is $C_{1-12}$ alkyl, $C_{1-12}$ alkoxy, $C_{3-12}$ cycloalkyl, $C_{5-12}$ aryl or $C_{5-12}$ aryl-$C_{1-6}$ alkyl, each of which may optionally be substituted with 1, 2 or 3 groups independently selected from F, Cl, Br, $CO_2H$, $CO_2$ ($C_{1-6}$ alkyl), CN, $CF_3$ or $CCl_3$; or Y is $NR^1R^2$; $R^1$ and $R^2$ are independently selected from H, $C_{1-12}$ alkyl, $C_{3-12}$ cycloalkyl, $C_{5-12}$ aryl, $C_{5-12}$ aryl-$C_{1-6}$ alkyl; or $R^1$ and $R^2$ may be joined to form a $C_{3-12}$ saturated heterocyclic group; $R^3$ is $C_{1-12}$ alkyl or $C_{3-12}$ cycloalkyl, each of which may optionally be substituted with 1, 2 or 3 groups independently selected from F, Cl, Br, $CO_2(C_{1-6}$ alkyl), CN, $CF_3$ or $CCl_3$; or $R^3$ is $C_{5-12}$ aryl or $C_{5-12}$ aryl-$C_{1-6}$ alkyl, each of which may optionally be substituted with 1, 2, 3, 4 or 5 groups selected from F, Cl, Br, $CO_2H$, $CO_2(C_{1-6}$ alkyl), CN, $CF_3$ or $CCl_3$. When $R^3$ is $C_{1-12}$ alkyl or $C_{3-12}$ cycloalkyl, it is typically substituted with 1, 2 or 3 groups as defined above. When $R^1$ and $R^2$ are joined to form a $C_{3-12}$ saturated heterocyclic group, it is meant that $R^1$ and $R^2$ together with the nitrogen atom form a saturated heterocyclic group containing any number of carbon atoms between 3 and 12 (e.g. $C_3$, $C_4$, $C_5$, $C_6$, $C_7$, $C_8$, $C_9$, $C_{10}$, $C_{11}$, $C_{12}$). The heterocyclic group may contain 1 or 2 heteroatoms (such as N, O or S) other than the nitrogen atom. Examples of $C_{3-12}$ saturated heterocyclic groups are pyrrolidinyl, piperidinyl, morpholinyl, piperazinyl, imidazolidinyl, azetidinyl and aziridinyl.

Blocking groups —O—X—Y and —$OR_3$ can be prepared from-OH groups by standard derivatizing procedures, such as reaction of the hydroxyl group with an acyl halide, alkyl halide, sulfonyl halide, etc. Hence, the oxygen atom in —O—X—Y is usually the oxygen atom of the hydroxyl group, while the —X—Y group in —O—X—Y usually replaces the hydrogen atom of the hydroxyl group.

Alternatively, the blocking groups may be accessible via a substitution reaction, such as a Mitsonobu-type substitution. These and other methods of preparing blocking groups from hydroxyl groups are well known.

Specific blocking groups for use in the invention are —$OC(O)CF_3$ [31] and a carbamate group $OC(O)NR^1R^2$, where $R^1$ and $R^2$ are independently selected from $C_{1-6}$ alkyl. Typically, $R^1$ and $R^2$ are both methyl i.e. the blocking group is —$OC(O)NMe_2$. Carbamate blocking groups have a stabilizing effect on the glycosidic bond and may be prepared under mild conditions.

A particularly preferred blocking group is —$OC(O)CH_3$ [30]. The proportion of 4- and/or 3-positions in the modified *Neisseria meningitidis* serogroup A saccharide that have this blocking group may vary. For example, the proportion of 4-positions that have blocking groups may be about 0%, at least 10%, 20%, 30%, 40%, 50%, 60%, 70%, 80%, 90%, 95% or about 100%, with at least 80% and about 100% being preferred. Similarly, the proportion of 3-positions that have blocking groups may be about 0%, at least 10%, 20%, 30%, 40%, 50%, 60%, 70%, 80%, 90%, 95% or about 100%, with at least 80% and about 100% being preferred. Typically, the proportion of 4- and 3-positions that have blocking groups is about the same at each position. In other words, the ratio of 4-positions that have blocking groups to 3-positions that have blocking groups is about 1:1. However, in some embodiments, the proportion of 4-positions that have blocking groups may vary relative to the proportion of 3-positions that have blocking groups. For example, the ratio of 4-positions that have blocking groups to 3-positions that have blocking groups may be 1:20, 1:19, 1:18, 1:17, 1:16, 1:15, 1:14, 1:13, 1:12, 1:11, 1:10, 1:9, 1:8, 1:7, 1:6, 1:5, 1:4, 1:3 or 1:2. Similarly, the ratio of 3-positions that have blocking groups to 4-positions that have blocking groups may be 1:20, 1:19, 1:18, 1:17, 1:16, 1:15, 1:14, 1:13, 1:12, 1:11, 1:10, 1:9, 1:8, 1:7, 1:6, 1:5, 1:4, 1:3 or 1:2.

Typical modified MenA saccharides contain n monosaccharide units, where at least h % of the monosaccharide units do not have-OH groups at both of positions 3 and 4. The value of h is 24 or more (e.g. 25, 26, 27, 28, 29, 30, 35, 40, 45, 50, 55, 60, 65, 70, 75, 80, 85, 90, 95, 98, 99 or 100) and is usually 50 or more. The absent-OH groups are blocking groups as defined above.

Other typical modified MenA saccharides comprise monosaccharide units, wherein at least s of the monosaccharide units do not have-OH at the 3 position and do not have-OH at the 4 position. The value of s is at least 1 (e.g. 2, 3, 4, 5, 6, 7, 8, 9, 10, 11, 12, 13, 14, 15, 16, 17, 18, 19, 20, 21, 22, 23, 24, 25, 26, 27, 28, 29, 30, 35, 40, 45, 50, 60, 70, 80, 90). The absent-OH groups are blocking groups as defined above.

Suitable modified MenA saccharides for use with the invention have the formula:

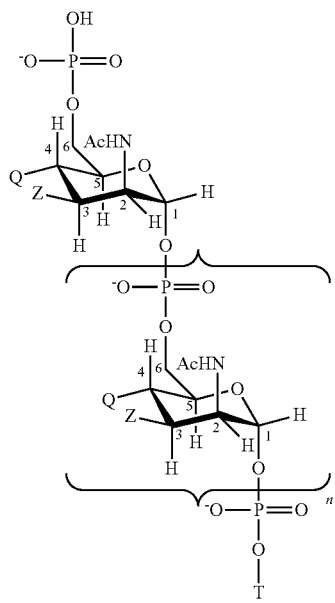

wherein
n is an integer from 1 to 100 (particularly an integer from 5 to 25, usually 15-25);
T is of the formula (A) or (B):

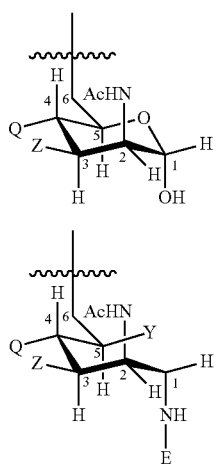

each Z group is independently selected from OH or a blocking group as defined above; and each Q group is independently selected from OH or a blocking group as defined above;
Y is selected from OH or a blocking group as defined above;
E is H or a nitrogen protecting group;
and wherein more than about 7% (e.g. 8%, 9%, 10% or more) of the Q groups are blocking groups. In some embodiments, the hydroxyl group attached at carbon 1 in formula (A) is replaced by a blocking group as defined above. In some embodiments, E in formula (B) is the point of attachment to the cyclooctyne group.

Each of the n+2 Z groups may be the same or different from each other. Likewise, each of the n+2 Q groups may be the same or different from each other. All the Z groups may be OH. Alternatively, at least 10%, 20, 30%, 40%, 50% or 60% of the Z groups may be OAc. Typically, about 70% of the Z groups are OAc, with the remainder of the Z groups being OH or blocking groups as defined above. At least about 7% of Q groups are blocking groups. Typically, at least 10%, 20%, 30%, 40%, 50%, 60%, 70%, 80%, 90% or even 100% of the Q groups are blocking groups.

Glucans

The saccharide may be a glucan. Glucans are glucose-containing polysaccharides found inter alia in fungal cell walls. The α-glucans include one or more α-linkages between glucose subunits, whereas β-glucans include one or more β-linkages between glucose subunits. The glucan used in accordance with the invention includes β linkages, and may contain only β linkages (i.e. no α linkages).

The glucan may comprise one or more β-1,3-linkages and/or one or more β-1,6-linkages. It may also comprise one or more β-1,2-linkages and/or β-1,4-linkages, but normally its only β linkages will be β-1,3-linkages and/or β-1,6-linkages.

The glucan may be branched or linear.

Full-length native β-glucans are insoluble and have a molecular weight in the megadalton range. It is preferred to use soluble glucans in conjugates of the invention. Solubilisation may be achieved by fragmenting long insoluble glucans. This may be achieved by hydrolysis or, more conveniently, by digestion with a glucanase (e.g. with a β-1,3-glucanase or a β-1,6-glucanase). As an alternative, short glucans can be prepared synthetically by joining monosaccharide building blocks.

Low molecular weight glucans are preferred, particularly those with a molecular weight of less than 100 kDa (e.g. less than 80, 70, 60, 50, 40, 30, 25, 20, or 15 kDa). It is also possible to use oligosaccharides e.g. containing 60 or fewer (e.g. 59, 58, 57, 56, 55, 54, 53, 52, 51, 50, 49, 48, 47, 46, 45, 44, 43, 42, 41, 40 39, 38, 37, 36, 35, 34, 33, 32, 31, 30, 29, 28, 27, 26, 25, 24, 23, 22, 21, 20, 19, 18, 17, 16, 15, 14, 13, 12, 11, 10, 9, 8, 7, 6, 5, 4) glucose monosaccharide units. Within this range, oligosaccharides with between 10 and 50 or between 20 and 40 monosaccharide units are preferred.

The glucan may be a fungal glucan. A 'fungal glucan' will generally be obtained from a fungus but, where a particular glucan structure is found in both fungi and non-fungi (e.g. in bacteria, lower plants or algae) then the non-fungal organism may be used as an alternative source. Thus the glucan may be derived from the cell wall of a *Candida*, such as *C. albicans*, or from *Coccidioides immitis*, *Trichophyton verrucosum*, *Blastomyces dermatidis*, *Cryptococcus neoformans*, *Histoplasma capsulatum*, *Saccharomyces cerevisiae*, *Paracoccidioides brasiliensis*, or *Pythiumn insidiosum*.

There are various sources of fungal β-glucans. For instance, pure β-glucans are commercially available e.g. pustulan (Calbiochem) is a β-1,6-glucan purified from

*Umbilicaria* papullosa. β-glucans can be purified from fungal cell walls in various ways. Reference 32, for instance, discloses a two-step procedure for preparing a water-soluble β-glucan extract from *Candida*, free from cell-wall mannan, involving NaClO oxidation and DMSO extraction. The resulting product ('*Candida* soluble β-D-glucan' or 'CSBG') is mainly composed of a linear β-1,3-glucan with a linear β-1,6-glucan moiety. Similarly, reference 33 discloses the production of GG-zym from Calbicans. Such glucans from *C. albicans*, include (a) β-1,6-glucans with β-1,3-glucan lateral chains and an average degree of polymerisation of about 30, and (b) β-1,3-glucans with β-1,6-glucan lateral chains and an average degree of polymerisation of about 4.

In some embodiments of the invention, the glucan is a β-1,3 glucan with some β-1,6 branching, as seen in e.g. laminarins. Laminarins are found in brown algae and seaweeds. The β(1-3):β(1-6) ratios of laminarins vary between different sources e.g. it is as low as 3:2 in *Eisenia* bicyclis laminarin, but as high as 7:1 in *Laminaria* digititata laminarin [34]. Thus the glucan used with the invention may have a β(1-3):β(1-6) ratio of between 1.5:1 and 7.5:1 e.g. about 2:1, 3:1, 4:1, 5:1, 6:1 or 7:1. Optionally, the glucan may have a terminal mannitol subunit, e.g. a 1,1-α-linked mannitol residue [35]. The glucan may also comprise mannose subunits.

In other embodiments, the glucan has exclusively or mainly β-1,3 linkages, as seen in curdlan. These glucans may elicit better protection than glucans comprising other linkages, particularly glucans comprising β-1,3 linkages and a greater proportion of β-1,6 linkages. Thus the glucan may be made solely of β-1,3-linked glucose residues (e.g. linear β-D-glucopyranoses with exclusively 1,3 linkages). Optionally, though, the glucan may include monosaccharide residues that are not β-1,3-linked glucose residues e.g. it may include B-1,6-linked glucose residues. The ratio of β-1,3-linked glucose residues to these other residues should be at least 8:1 (e.g. ≥9:1, ≥10:1, ≥11:1, ≥12:1, ≥13:1, ≥14:1, ≥15:1, ≥16:1, ≥17:1, ≥18:1, ≥19:1, ≥20:1, ≥25:1, ≥30:1, ≥35:1, ≥40:1, ≥45:1, ≥50:1, ≥75:1, ≥100:1, etc.) and/or there are one or more (e.g. ≥1, ≥2, ≥3, ≥4, ≥5, ≥6, ≥7, ≥8, ≥9, ≥10, ≥11, ≥12, etc.) sequences of at least five (e.g. ≥5, ≥6, ≥7, ≥8, ≥9, ≥10, ≥11, ≥12, ≥13, ≥14, ≥15, ≥16, ≥17, ≥18, ≥19, ≥20, ≥30, ≥40, ≥50, ≥60, etc.) adjacent non-terminal residues linked to other residues only by β-1,3 linkages. By "non-terminal" it is meant that the residue is not present at a free end of the glucan. In some embodiments, the adjacent non-terminal residues may not include any residues at which the cyclooctyne group is attached. The presence of five adjacent non-terminal residues linked to other residues only by β-1,3 linkages may provide a protective antibody response, e.g. against *C. albicans*.

In further embodiments, a conjugate may include two different glucans e.g. a first glucan having a β(1-3):β(1-6) ratio of between 1.5:1 and 7.5:1, and a second glucan having exclusively or mainly β-1,3 linkages. For instance a conjugate may include both a laminarin glucan and a curdlan glucan.

Where a β-glucan includes both β-1,3 and β-1,6 linkages at a desired ratio and/or sequence then this glucan may be found in nature (e.g. a laminarin), or it may be made artificially. For instance, it may be made by chemical synthesis, in whole or in part. Methods for the chemical synthesis of β-1,3/β-1,6 glucans are known, for example from references 36-46. β-glucan including both β-1,3 and β-1,6 linkages at a desired ratio may also be made starting from an available glucan and treating it with a β-1,6-glucanase (also known as glucan endo-1,6-β-glucosidase, 1,6-β-D-glucan glucanohydrolase, etc.; EC 3.2.1.75) or a β-1,3-glucanase (such as an exo-1,3-glucanase (EC 3.2.1.58) or an endo-1,3-glucanase (EC 3.2.1.39) until a desired ratio and/or sequence is reached.

When a glucan containing solely β-1,3-linked glucose is desired then β-1,6-glucanase treatment may be pursued to completion, as β-1,6-glucanase will eventually yield pure β-1,3 glucan. More conveniently, however, a pure β-1,3-glucan may be used. These may be made synthetically, by chemical and/or enzymatic synthesis e.g. using a (1→3)-β-D-glucan synthase, of which several are known from many organisms (including bacteria, yeasts, plants and fungi). Methods for the chemical synthesis of β-1,3 glucans are known, for example from references 47-50. As a useful alternative to synthesis, a natural β-1,3-glucan may be used, such as a curdlan (linear β-1,3-glucan from an *Agrobacterium* previously known as *Alcaligenes faecalis* var. myxogenes; commercially available e.g. from Sigma-Aldrich catalog C7821) or paramylon (β-1,3-glucan from *Euglena*). Organisms producing high levels of β-1,3-glucans are known in the art e.g. the *Agrobacterium* of refs. 51 & 52, or the *Euglena gracilis* of ref. 53.

Laminarin and curdlan are typically found in nature as high molecular weight polymers e.g. with a molecular weight of at least 100 kDa. They are often insoluble in aqueous media. In their natural forms, therefore, they are not well suited to immunisation. Thus the invention may use a shorter glucan e.g. those containing 60 or fewer glucose monosaccharide units (e.g. 59, 58, 57, 56, 55, 54, 53, 52, 51, 50, 49, 48, 47, 46, 45, 44, 43, 42, 41, 40 39, 38, 37, 36, 35, 34, 33, 32, 31, 30, 29, 28, 27, 26, 25, 24, 23, 22, 21, 20, 19, 18, 17, 16, 15, 14, 13, 12, 11, 10, 9, 8, 7, 6, 5, 4). A glucan having a number of glucose residues in the range of 2-60 may be used e.g. between 10-50 or between 20-40 glucose units. A glucan with 25-30 glucose residues is particularly useful. Suitable glucans may be formed e.g. by acid hydrolysis of a natural glucan, or by enzymatic digestion e.g. with a glucanase, such as a β-1,3-glucanase. A glucan with 11-19, e.g. 13-19 and particularly 15 or 17, glucose monosaccharide units is also useful. In particular, glucans with the following structures (A) or (B) are specifically envisaged for use in the present invention:

(A)

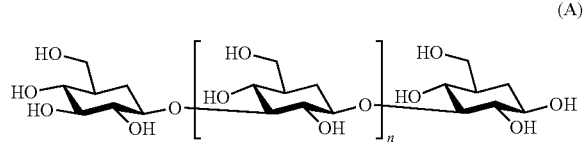

wherein n+2 is in the range of 2-60, e.g. between 10-50 or between 2-40. Preferably, n+2 is in the range of 25-30 or 6-19, e.g. 6 or 13-17. The inventors have found that n+2=6 is suitable. n+2=15 may also be suitable

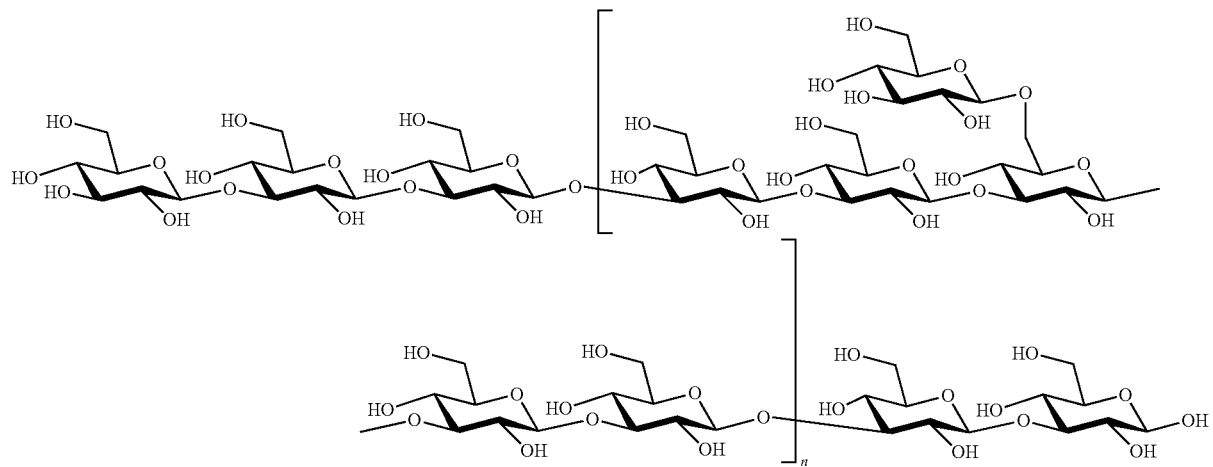

wherein n is in the range of 0-9, e.g. between 1-7 or between 2-6. Preferably, n is in the range of 3-4 or 1-3. The inventors have found that n=2 is suitable.

In some embodiments, the glucan is a single molecular species. In these embodiments, all of the glucan molecules are identical in terms of sequence. Accordingly, all of the glucan molecules are identical in terms of their structural properties, including molecular weight etc. Typically, this form of glucan is obtained by chemical synthesis, e.g. using the methods described above. For example, reference 48 describes the synthesis of a single β-1,3 linked species. Alternatively, in other embodiments, the glucan may be obtained from a natural glucan, e.g. a glucan from *L. digitata*, *Agrobacterium* or *Euglena* as described above, with the glucan being purified until the required single molecular species is obtained. Natural glucans that have been purified in this way are commercially available. A glucan that is a single molecular species may be identified by measuring the polydispersity (Mw/Mn) of the glucan sample. This parameter can conveniently be measured by SEC-MALLS, for example as described in reference 54. Suitable glucans for use in this embodiment of the invention have a polydispersity of about 1, e.g. 1.01 or less.

Solubility of natural glucans, such as curdlan, can be increased by introducing ionic groups (e.g. by sulfation, particularly at O-6 in curdlan). Such modifications may be used with the invention, but are ideally avoided as they may alter the glucan's antigenicity.

When the saccharide is a glucan, it is typically a laminarin.

S. pneumoniae Capsular Saccharides

As discussed above, the saccharide may also be a bacterial capsular saccharide. Further exemplary bacterial capsular saccharides include those from *S. pneumoniae*. When the saccharide is a capsular saccharides from *S. pneumoniae*, it is typically from one of the following pneumococcal serotypes: 1, 2, 3, 4, 5, 6A, 6B, 7F, 8, 9N, 9V, 10A, 11A, 12F, 14, 15B, 17F, 18C, 19A, 19F, 20, 22F, 23F and 33F, preferably from 1, 5, 6B, 14, 19F and 23F. Capsular polysaccharides from *S. pneumoniae* comprise repeating oligosaccharide units which may contain up to 8 sugar residues. The oligosaccharide units for the main *S. pneumoniae* serotypes are described in refs 55 and 56.

S. aureus Capsular Saccharides

Further exemplary bacterial capsular saccharides include those from *S. aureus*, particularly the capsular polysaccharides of *S. aureus* type 5 and type 8. The structures of type 5 and type 8 capsular polysaccharides were described in references 57 and 58 as:

Type 5

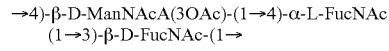

Type 8

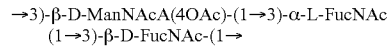

Recent NMR spectroscopy data has led to a revision of these structures to:

Type 5

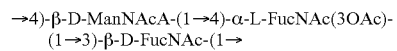

Type 8

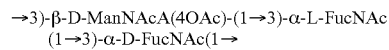

The polysaccharide may be chemically modified relative to the capsular polysaccharide as found in nature.

For example, the polysaccharide may be de-O-acetylated (partially or fully), de-N-acetylated (partially or fully), N-propionated (partially or fully), etc. De-acetylation may occur before, during or after conjugation, but typically occurs before conjugation. The effect of de-acetylation etc. can be assessed by routine assays. For example, the relevance of O-acetylation on *S. aureus* type 5 or type 8 capsular polysaccharides is discussed in reference 60. The native polysaccharides are said in this document to have 75% O-acetylation. These polysaccharides induced antibodies to both the polysaccharide backbone and O-acetyl groups. Polysaccharides with 0% O-acetylation still elicited antibodies to the polysaccharide backbone. Both types of antibody were opsonic against *S. aureus* strains that varied in their O-acetyl content. Accordingly, the type 5 or type 8 capsular polysaccharides used in the present invention may have between 0 and 100% O-acetylation.

The degree of O-acetylation of the polysaccharide can be determined by any method known in the art, for example, by proton NMR (e.g. as described in references 61, 62, 63 or 64). A further method is described in reference 65. Similar methods may be used to determine the degree of N-acetylation of the polysaccharide. O-acetyl groups may be removed by hydrolysis, for example by treatment with a base such as anhydrous hydrazine or NaOH [60]. Similar methods may be used to remove N-acetyl groups. To maintain high levels of O-acetylation on type 5 and/or 8 capsular polysaccharides, treatments that lead to hydrolysis of the O-acetyl groups are minimised, e.g. treatments at extremes of pH.

Capsular polysaccharides can be purified by known techniques, as described in the references herein. A typical process involves phenol-ethanol inactivation of *S. aureus* cells, centrifugation, lysostaphin treatment, RNase/DNase treatment, centrifugation, dialysis, protease treatment, further dialysis, filtration, precipitation with ethanol/$CaCl_2$), dialysis, freeze-drying, anion exchange chromatography, dialysis, freeze-drying, size exclusion chromatography, dialysis and freeze-drying [67]. An alternative process involves autoclaving *S. aureus* cells, ultrafiltration of the polysaccharide-containing supernatant, concentration, lyophilisation, treatment with sodium metaperiodate to remove teichoic acid, further ultrafiltration, diafiltration, high performance size exclusion liquid chromatography, dialysis and freeze-drying [68].

The invention is not limited to polysaccharides purified from natural sources, however, and the polysaccharides may be obtained by other methods, such as total or partial synthesis.

Other Bacterial Capsular Saccharides

Further exemplary bacterial capsular saccharides include those from *Haemophilus influenzae* Type b, *Salmonella enterica Typhi* Vi and *Clostridium difficile*.

S. Pyogenes (Group A *Streptococcus* or GAS) Carbohydrate

The invention may also use non-capsular bacterial saccharides. An exemplary non-capsular bacterial saccharides is the *S. pyogenes* GAS carbohydrate (also known as the GAS cell wall polysaccharide, or GASP). This saccharide features a branched structure with an L-rhamnopyranose (Rhap) backbone consisting of alternating alpha-(1→2) and alpha-(1→3) links and D-N-acetylglucosamine (GlcpNAc) residues beta-(1→3)-connected to alternating rhamnose rings ([69]).

The GAS carbohydrate will generally be in its native form, but it may have been modified. For example, the saccharide may be shorter than the native GAS carbohydrate, or may be chemically modified.

Thus the saccharide used according to the invention may be a substantially full-length GAS carbohydrate, as found in nature, or it may be shorter than the natural length. Full-length polysaccharides may be depolymerised to give shorter fragments for use with the invention e.g. by hydrolysis in mild acid, by heating, by sizing chromatography, etc. A short fragment thought to correspond to the terminal unit on the GAS carbohydrate has been proposed for use in a vaccine [70]. Accordingly, short fragments are envisaged in the present invention. However, it is preferred to use saccharides of substantially full-length. The GAS carbohydrate typically has a molecular weight of about 10, in particular about 7.5-8.5 kDa. Molecular masses can be measured by HPLC, for example SEC-HPLC using a TSK Gel G3000SW column (Sigma) relative to pullulan standards, such as those available from Polymer Standard Service [71].

The saccharide may be chemically modified relative to the GAS carbohydrate as found in nature. For example, the saccharide may be de-N-acetylated (partially or fully), N-propionated (partially or fully), etc. The effect of de-acetylation etc., for example on immunogenicity, can be assessed by routine assays.

Derivatization

The present invention relates in part to a method of derivatizing a saccharide comprising attaching an eight-membered cycloalkyne group to the saccharide.

The eight-membered cycloalkyne group is attached to the saccharide by a covalent linkage. Typically, the eight-membered cycloalkyne group is attached via a spacer. The eight-membered cycloalkyne group is typically at a terminus of the spacer. The other terminus of the spacer has a functional group for attachment to the saccharide. The nature of the functional group will depend on the saccharide, in particular on the group or groups available on the saccharide for attachment. Attachment of the eight-membered cycloalkyne group can be carried out using any suitable method depending on the nature of the saccharide and, when a spacer is used, the functional group on the spacer.

For example, if the saccharide contains an amine, the spacer can include any functional group that allows attachment to an amine (e.g. a succinimidyl ester). Similarly, if the saccharide contains an aldehyde, the spacer can include any functional group that allows attachment to an aldehyde (e.g. an amine).

In some embodiments, the eight-membered cycloalkyne group includes one or more nitrogen atoms, such as 1, 2 or 3 nitrogen atoms. In some embodiments, the eight-membered cycloalkyne group is fused to one or more other ring systems, such as cyclopropane or benzene. In one preferred embodiment, the eight-membered cycloalkyne group is fused to a cyclopropane group. In another preferred embodiment, the eight-membered cycloalkyne group is fused to two benzene groups. In most preferred embodiments, the eight-membered cycloalkyne group is a cyclooctyne group.

In one embodiment, the attachment is carried out using a compound having the formula $X_1$-L-$X_2$, where $X_1$ is the eight-membered cycloalkyne group and $X_2$-L is the spacer. In these embodiments, $X_2$ may be any group that can react with a functional group on the saccharide, and L is a linking moiety in the spacer.

In some preferred embodiments, $X_2$ is N-oxysuccinimide. This group is suitable for attachment to an amine on a saccharide. In other embodiments, $X_2$ may be an amine group, which is suitable for attachment to an aldehyde on a saccharide. L may be a straight chain alkyl with 1 to 10 carbon atoms (e.g. $C_1$, $C_2$, $C_3$, $C_4$, $C_5$, $C_6$, $C_7$, $C_8$, $C_9$, $C_{10}$) e.g. —$(CH_2)_4$— or —$(CH_2)_3$—. L typically has formula -$L^3$-$L^2$-$L^1$-, in which $L^1$ is carbonyl, $L^2$ is a straight chain alkyl with 1 to 10 carbon atoms (e.g. $C_1$, $C_2$, $C_3$, $C_4$, $C_5$, $C_6$, $C_7$, $C_8$, $C_9$, $C_{10}$) e.g. —$(CH_2)_4$— or —$(CH_2)_5$— or $L^1$ is absent, and $L^3$ is —NHC(O)—, carbonyl or —O($CH_3$)—.

In one preferred embodiment, $L^1$ is carbonyl, $L^2$ is —$(CH_2)_5$— and $L^3$ is —NHC(O)—. In another preferred embodiment, $L^1$ is carbonyl, $L^2$ is —$(CH_2)_4$— and $L^3$ is carbonyl. In another preferred embodiment, $L^1$ is carbonyl, $L^2$ is absent and $L^3$ is —O($CH_3$)—.

In one embodiment, $X_1$ is:

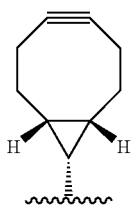 [SMILES: *[C@H]1[C@H]2CCC#CCC[C@@H]12]

In another embodiment, $X_1$ is:

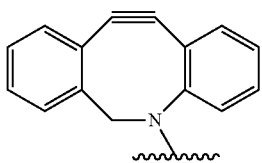 [SMILES: *N1Cc2ccccc2C#Cc2ccccc21]

Preferably, $X_1$ is:

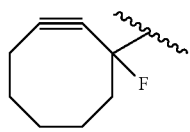

A preferred compound having the formula $X_1$-L-$X_2$ is:

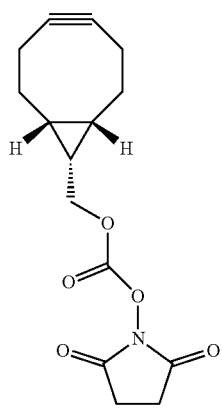

Another preferred compound having the formula $X_1$-L-$X_2$ is:

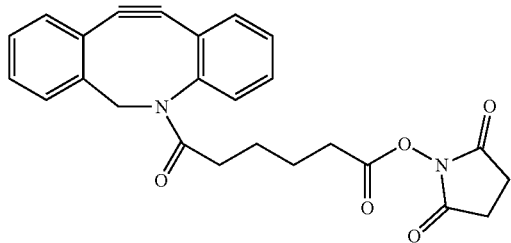 [SMILES: O=C(CCCCC(=O)N1Cc2ccccc2C#Cc2ccccc21)ON1C(=O)CCC1=O]

A particularly preferred compound having the formula $X_1$-L-$X_2$ is:

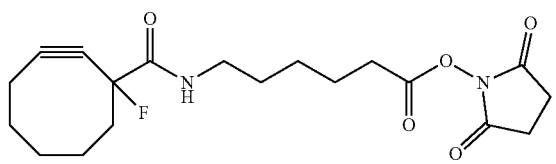 [SMILES: O=C(CCCCCNC(=O)C1(F)C#CCCCCC1)ON1C(=O)CCC1=O]

Derivatization of the saccharide may be required to introduce functional groups such as amines and aldehydes. In some embodiments, attachment of the eight-membered cycloalkyne group to the saccharide is preceded by oxidation of the saccharide in order to introduce an aldehyde group into at least one saccharide residue in the saccharide. This step may involve the introduction of more than one aldehyde group into the saccharide.

For example, GBS capsular saccharides do not include an aldehyde group in their natural form, and so it is typically generated before attachment of the cyclooctyne group by oxidation (e.g. periodate oxidation) of a portion (e.g. between 5 and 40%, particularly between 10 and 30%, preferably about 20%) of the saccharide's sialic acid residues [72]. Alternatively, if the method uses a serotype V capsular saccharide that is desialylated, then an aldehyde group may be generated in this saccharide before attachment of the eight-membered cycloalkyne group by oxidation (e.g. periodate oxidation) of a portion (e.g. between 5 and 40%, particularly between 10 and 30%, preferably about 20%) of the saccharide's galactose residues [10].

Typical reactions to produce aldehydes include the use of periodate salts, and particularly meta-periodates (e.g. sodium or potassium meta-periodate e.g. $NaIO_4$), to oxidise hydroxyl groups [73]. The skilled person would be capable of identifying suitable conditions for oxidation.

Oxidation of the saccharide may be followed by a step of reductive amination, for example if it is desirable to provide an amine on the saccharide for attachment to a spacer.

Reductive amination is a standard technique in organic chemistry. In one embodiment, an aldehyde group in the saccharide residue reacts with an amine group in the spacer. This can conveniently be achieved by combining the polysaccharide with the spacer in the presence of an appropriate reducing agent (e.g. cyanoborohydrides, such as sodium cyanoborohydride $NaBH_3CN$; borane-pyridine; sodium triacetoxyborohydride; borohydride exchange resin; etc.). In another embodiment, an aldehyde group is converted into an amine group by reductive amination to provide an amine group for attachment of the spacer. The reductive amination involves either ammonia or a primary amine ($NH_2R$). This can conveniently be achieved by using an ammonium salt (e.g. ammonium chloride) in combination with an appropriate reducing agent (e.g. as listed above). The skilled person would be capable of identifying suitable conditions for reductive amination. For example, the inventors have found that treatment of polysaccharide at 10 mg/ml with carrier protein at a 4:1 polysaccharide: protein ratio (w/w) and $NaBH_3CN$ at a 2:1 polysaccharide: $NaBH_3CN$ ratio is suitable.

When a spacer is used, the saccharide derivative will comprise a spacer moiety. The spacer moiety may include atoms such as carbon, hydrogen, oxygen and/or nitrogen. Spacers that comprise carbon and hydrogen are typical, and spacers that further comprise oxygen and/or nitrogen are also typically used. Spacers that include nitrogen atoms may include a carbon atom bonded to a nitrogen atom, which in turn is bonded to a second carbon atom (—C—N—C—). Spacers that include an oxygen atom typically include it as part of a carbonyl group. Spacer moieties with a molecular weight of between 30-500 Da are typical. Spacers containing two carbonyl groups are also typical.

A useful spacer moiety may be —NH—C(O)—$(CH_2)_n$—NH—C(O)—, wherein n is 1, 2, 3, 4, 5, 6, 7, 8, 9 or 10. The value of n is typically 5. The terminal —NH— in this spacer is usually attached to a carbon atom from the polysaccharide moiety. The terminal —C(O)— in this spacer is usually attached to the cyclooctyne group. A preferred spacer moiety can conveniently be introduced by a process involving:

reductive amination of the aldehyde in the oxidised saccharide residue; reaction of the resulting —NH$_2$ group with a bifunctional spacer that is a diester (e.g. a disuccinimidyl ester) of a dioic acid (e.g. of adipic acid, HOOC—(CH$_2$)$_4$—COOH); and reductive amination of the product ([74]).

Other chemistries that can be used to attach a spacer to a —NH$_2$ group in the saccharide, include:
- acryloylation (e.g. by reaction with acryloyl chloride), followed by Michael-type addition to either the ε—NH$_2$ or to a —SH [75]. The resulting spacer moiety is —NH—C(O)—(CH$_2$)$_2$— (propionamido).
- reaction with a haloacylhalide, followed by reaction with the ε—NH$_2$ or to a —SH [76]. The spacer moiety is —NH—C(O)—CH$_2$—.

The method of derivatizing a saccharide according to the invention may give the saccharide as described below.

The Saccharide Derivative

The invention provides a saccharide derivative comprising an eight-membered cycloalkyne group. The saccharide derivative may include any saccharide and, where appropriate, spacer, as outlined above. The invention also provides a saccharide derivative obtained or obtainable by the method outlined above. The saccharide derivative is not a naturally occurring saccharide.

Preferred saccharide derivatives include a capsular saccharide from *Streptococcus agalactiae* ("GBS"). In particularly preferred embodiments, the saccharide is a capsular saccharide from *Streptococcus agalactiae* ("GBS") serotype II or V. In one embodiment, the saccharide derivative is a GBS derivative having the following structure:

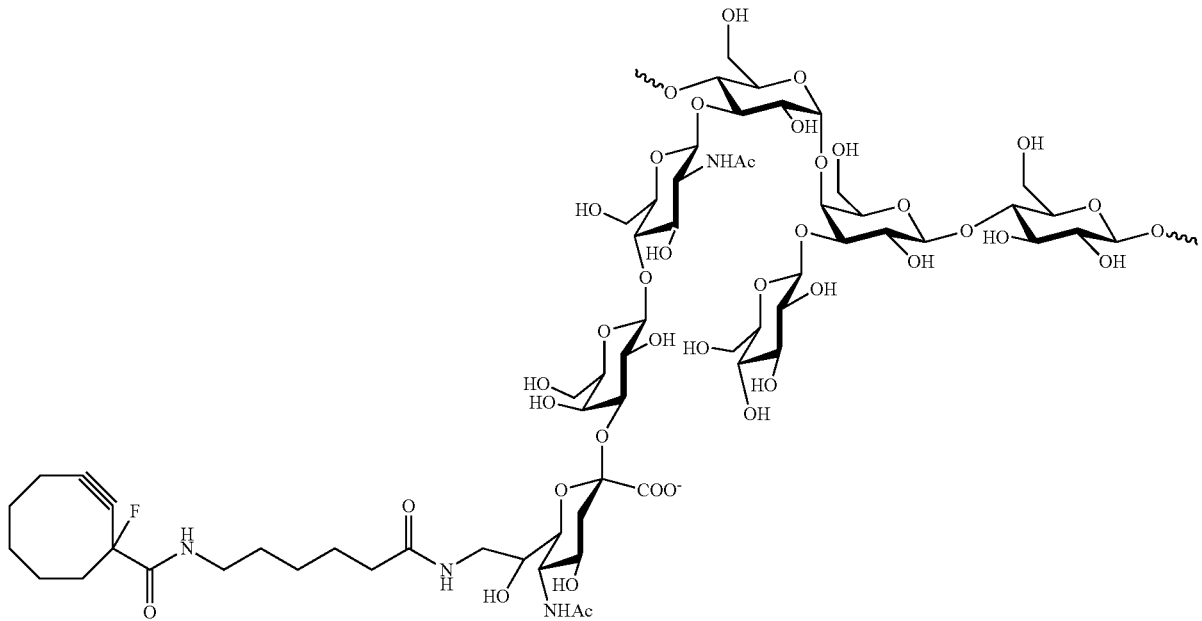

In another embodiment, the saccharide derivative is a GBS derivative having the following structure:

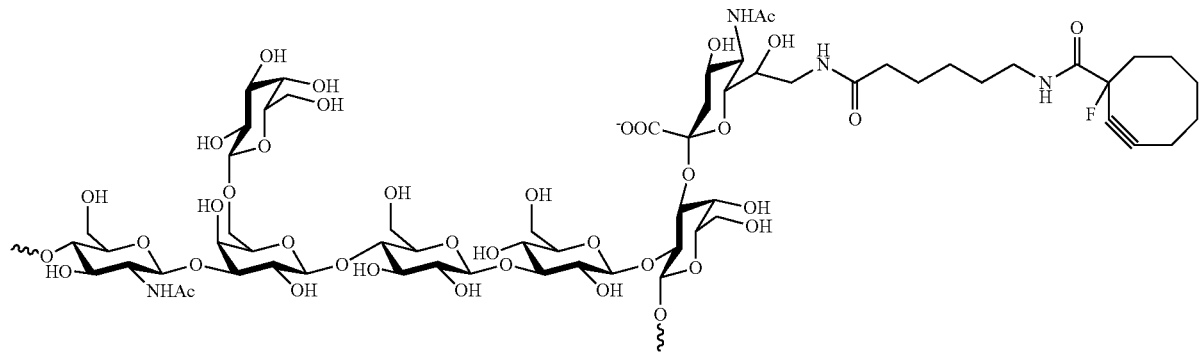

Conjugation Method

The invention relates in part to a method of conjugating a saccharide derivative as defined above to an azide-containing moiety, comprising reacting the eight-membered cycloalkyne group with the azide to form a triazole linkage. In some embodiments, the saccharide derivative used in the method of conjugation is produced according to the methods described above. In particular, the saccharide derivative may be produced by attaching an eight-membered cycloalkyne group to the saccharide. The method of conjugation is typically carried out in the absence of a metal catalyst, such as a copper catalyst.

The inventors have found that a suitable conjugation method involves mixing protein (typically at a concentration of 5 mg/ml) in phosphate buffered saline (PBS), with saccharide (typically solubilized in water at a concentration of about 25-30 mg/ml). Typically, the mixture of protein and saccharide will be stirred for about 6-12 hours at room temperature.

The method of conjugating a saccharide derivative to an azide-containing moiety occurs via a [3+2] cycloaddition reaction. This reaction is facilitated by the ring strain in the eight-membered cycloalkyne, which promotes the azide-alkyne cycloaddition reaction in the absence of a copper catalyst. The inventors have found that this method of conjugation is particularly efficient, and is capable of producing conjugates in higher than were achievable using classical conjugation methods. General methods for conjugation using a [3+2] cycloaddition reaction are known in the art and are disclosed in reference 77.

The method of conjugating a saccharide derivative to an azide-containing moiety may give a conjugate as described below.

Azide-Containing Moiety

Typically, the azide-containing moiety is a carrier molecule, such as a protein. The azide-containing moiety can be made according to methods known in the art, for example the methods disclosed in reference 78.

Useful carrier proteins include bacterial toxins or toxoids, such as diphtheria toxoid or tetanus toxoid. Fragments of toxins or toxoids can also be used e.g. fragment C of tetanus toxoid [79]. For example, the CRM197 mutant of diphtheria toxin [80-82] is a useful with the invention. Other suitable carrier proteins include the *N. meningitidis* outer membrane protein [83], synthetic peptides [84,85], heat shock proteins [86,87], pertussis proteins [88,89], cytokines [90], lymphokines [90], hormones [90], growth factors [90], human serum albumin (preferably recombinant), artificial proteins comprising multiple human CD4 T cell epitopes from various pathogen-derived antigens such as N19 [92], protein D from *H. influenzae* [93,94], pneumococcal surface protein PspA [95], pneumolysin [96], iron-uptake proteins [97], toxin A or B from *C. difficile* [98], recombinant *Pseudomonas aeruginosa* exoprotein A (rEPA) [99], a GBS protein [100], etc. In preferred embodiments, the carrier protein is a GBS protein, such as GBS67 and GBS80 [101].

Typically, the azide-containing moiety includes a spacer. The azide is typically present as a terminal group in the azide-containing moiety, such that it is available to take part in the conjugation reactions as described herein.

Spacers are used to attach an azide group to the moiety. Methods for attaching a spacer to a carrier molecule, such as a protein, are known in the art (see e.g. reference 78).

The spacer may be a straight chain alkyl with 1 to 10 carbon atoms (e.g. $C_1$, $C_2$, $C_3$, $C_4$, $C_5$, $C_6$, $C_7$, $C_8$, $C_9$, $C_{10}$) e.g. —$(CH_2)_4$— or —$(CH_2)_3$—. In some preferred embodiments, the spacer has the formula —$[(CH_2)_2O]_n$—, where n is 1, 2, 3, 4, 5, 6, 7, 8, 9 or 10. Suitably, n is 3.

When a spacer is used, the azide-containing moiety will comprise a spacer moiety. The spacer moiety may include atoms such as carbon, hydrogen, oxygen and/or nitrogen. Spacers that comprise carbon and hydrogen are typical, and spacers that further comprise oxygen and/or nitrogen are also typically used. Spacers that include nitrogen atoms may include a carbon atom bonded to a nitrogen atom, which in turn is bonded to a second carbon atom (—C—N—C—). Spacers that include an oxygen atom typically include it as part of a carbonyl group. Spacer moieties with a molecular weight of between 30-500 Da are typical. Spacers containing two carbonyl groups are also typical. A particularly useful spacer moiety includes —$[(CH_2)_2O]_n$—, where n is 1, 2, 3, 4, 5, 6, 7, 8, 9 or 10. Suitably, n is 3.

In preferred embodiments, the azide-containing moiety contains one or more derivatized amino acids, such as one or more derivatized tyrosine residues. Suitable methods for derivatizing tyrosine residues are described in PCT/US2012/045549. In preferred embodiments, the azide-containing moiety is a carrier protein in which the azide is attached to the protein via a spacer. The azide-containing moiety may be a carrier protein in which the azide is attached to a derivatized tyrosine residue on the protein via a spacer. The inventors have found that attaching the azide to a carrier protein via a tyrosine residue on the protein is particularly preferred. In some embodiments, the azide-containing moiety is a carrier protein containing at least one derivatized tyrosine residue having the following structure, wherein the azide is attached via the 3H-1,2,4-triazole-3,5 (4H)-dione:

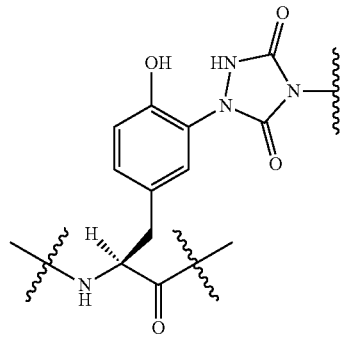 [SMILES: *N[C@@H](Cc1ccc(O)c(-n2[nH]c(=O)n(*)c2=O)c1)C(*)=O]

For example, the azide-containing moiety may be a carrier protein containing at least one derivatized tyrosine residue having the following structure:

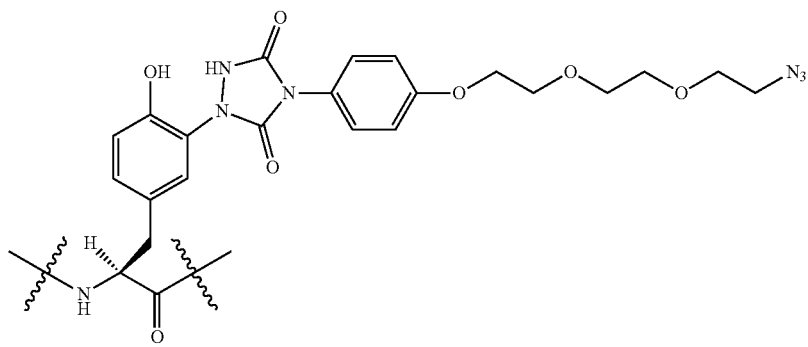 [SMILES: *N[C@@H](Cc1ccc(O)c(-n2[nH]c(=O)n(-c3ccc(OCCOCCOCCN=[N+]=[N-])cc3)c2=O)c1)C(*)=O]

The invention also provides azide-containing moieties as described herein.

Conjugates

The invention relates in part to a conjugate of a saccharide derivative as defined above and an azide-containing moiety as defined above, wherein the conjugate has the formula R-S-T, wherein R comprises a residue of the saccharide derivative, S is a triazole group fused to an eight-membered cycloalkyl group and T comprises a residue of the azide-containing moiety.

In some embodiments, the eight-membered cycloalkyl group includes one or more nitrogen atoms, such as 1, 2 or 3 nitrogen atoms. In some embodiments, the eight-membered cycloalkyl group is fused to one or more other ring systems in addition to the triazole group, such as cyclopropane or benzene. In one preferred embodiment, the eight-membered cycloalkyne group is fused to a cyclopropane group in addition to the triazole group. In another preferred embodiment, the eight-membered cycloalkyne group is fused to two benzene groups in addition to the triazole group.

In a preferred embodiment, R-S-T is:

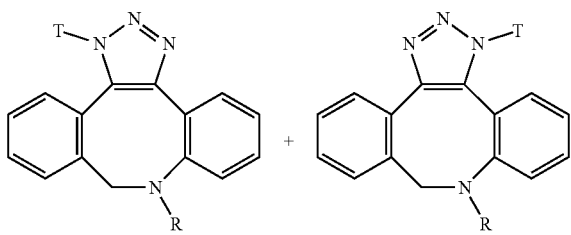

In another preferred embodiment, R-S-T is:

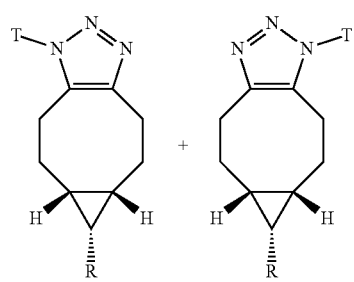

In a most preferred embodiment R-S-T is:

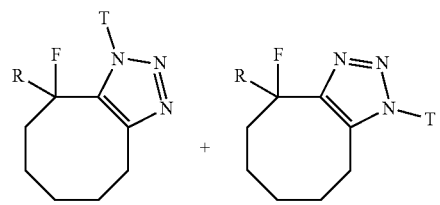

The moiety is typically a carrier molecule, such as a protein. Suitable carrier proteins are described above. The conjugate may include a spacer in the residue of the saccharide derivative between the saccharide and S. For example, the spacer can be a spacer as described above for the saccharide derivative. In addition or alternatively, the conjugate may include a spacer in the residue of the azide-containing moiety between the moiety and S. For example, the spacer can be a spacer as described above for the azide-containing moiety. Typically, the conjugate will include a spacer in the residue of the saccharide derivative between the saccharide and S and a spacer in the residue of the azide-containing moiety between the moiety and S.

In a particularly preferred embodiment, the conjugate includes GBS serotype V saccharide conjugated to GBS80 protein. In another particularly preferred embodiment, the conjugate includes GBS serotype II saccharide conjugated to GBS80 protein. In another particularly preferred embodiment, the conjugate includes GBS serotype V saccharide conjugated to GBS67 protein. In another particularly preferred embodiment, the conjugate includes OBS serotype II saccharide conjugated to GBS67 protein.

For example, the conjugate may have the following structure:

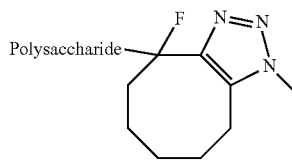 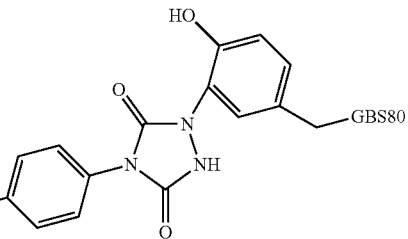

In some embodiments, conjugates may have excess carrier protein (w/w) or excess saccharide (w/w) e.g. in the ratio range of 1:5 to 5:1. The conjugate may include small amounts of free (i.e. unconjugated) carrier protein. When a given carrier protein is present in both free and conjugated form in a composition of the invention, the unconjugated form is preferably no more than 5% of the total amount of the carrier protein in the composition as a whole, and more preferably present at less than 2% (by weight). When the conjugate is comprised within a pharmaceutical composition of the invention, the composition may also comprise free carrier protein as immunogen [102] After conjugation, free and conjugated antigens can be separated. There are many suitable methods e.g. hydrophobic chromatography, tangential ultrafiltration, diafiltration, etc. [see also refs 103, 104 etc.].

Combinations of Conjugates and Other Antigens

As well as providing individual conjugates as described above, the invention provides s composition comprising a conjugate of the invention and one or more further antigens. The composition is typically an immunogenic composition.

The composition of the invention may further comprise one or more further antigens, including additional bacterial, viral or parasitic antigens. These may be selected from the following:
- a protein antigen from N. meningitidis serogroup B, such as those in refs. 105 to 111, with protein '287' (see below) and derivatives (e.g. 'ΔG287') being particularly preferred.
- an outer-membrane vesicle (OMV) preparation from N. meningitidis serogroup B, such as those disclosed in refs. 112, 113, 114, 115 etc.
- a saccharide antigen from N. meningitidis serogroup A. C. W135 and/or Y, such as the oligosaccharide disclosed in ref. 116 from serogroup C or the oligosaccharides of ref. 117.
- a saccharide antigen from Streptococcus pneumoniae [e.g. refs. 118-120; chapters 22 & 23 of ref. 127].
- an antigen from hepatitis A virus, such as inactivated virus [e.g. 121, 122; chapter 15 of ref. 127].
- an antigen from hepatitis B virus, such as the surface and/or core antigens [e.g. 122,123; chapter 16 of ref. 127].
- an antigen from hepatitis C virus [e.g. 124].
- an antigen from Bordetella pertussis, such as pertussis holotoxin (PT) and filamentous haemagglutinin (FHA) from B. pertussis, optionally also in combination with pertactin and/or agglutinogens 2 and 3 [e.g. refs. 125 & 126; chapter 21 of ref. 127].
- a diphtheria antigen, such as a diphtheria toxoid [e.g. chapter 13 of ref. 127].
- a tetanus antigen, such as a tetanus toxoid [e.g. chapter 27 of ref. 127].
- a saccharide antigen from Haemophilus influenzae B [e.g. chapter 14 of ref. 127]
- an antigen from N. gonorrhoeae [e.g. 105, 106, 107].
- an antigen from Chlamydia pneumoniae [e.g. 128, 129, 130, 131, 132, 133, 134].
- an antigen from Chlamydia trachomatis [e.g. 135].
- an antigen from Porphyromonas gingivalis [e.g. 136].
- polio antigen(s) [e.g. 137, 138; chapter 24 of ref. 127] such as IPV.
- rabies antigen(s) [e.g. 139] such as lyophilised inactivated virus [e.g. 140, RabAvert™ ].
- measles, mumps and/or rubella antigens [e.g. chapters 19, 20 and 26 of ref. 127].
- influenza antigen(s) [e.g. chapters 17 & 18 of ref. 127], such as the haemagglutinin and/or neuraminidase surface proteins.
- an antigen from Moraxella catarrhalis [e.g. 141].
- an antigen from Streptococcus pyogenes (group A streptococcus) [e.g. 142, 143, 144].
- an antigen from Streptococcus agalactiae (group B streptococcus) [e.g. 145-147].
- an antigen from S. epidermidis [e.g. type I, II and/or III saccharide obtainable from strains ATCC-31432, SE-360 and SE-10 as described in refs. 148, 149 and 150.

Where a saccharide or carbohydrate antigen is used, it is preferably conjugated to a carrier in order to enhance immunogenicity. Conjugation of H. influenzae B, meningococcal and pneumococcal saccharide antigens is well known.

Toxic protein antigens may be detoxified where necessary (e.g. detoxification of pertussis toxin by chemical and/or genetic means [126]).

Where a diphtheria antigen is included in the composition it is preferred also to include tetanus antigen and pertussis antigens. Similarly, where a tetanus antigen is included it is preferred also to include diphtheria and pertussis antigens. Similarly, where a pertussis antigen is included it is preferred also to include diphtheria and tetanus antigens.

Antigens may be adsorbed to an aluminium salt. Where there is more than one conjugate in a composition, not all conjugates need to be adsorbed.

Antigens in the composition will typically be present at a concentration of at least 1 µg/ml each. In general, the concentration of any given antigen will be sufficient to elicit an immune response against that antigen.

As an alternative to using proteins antigens in the composition of the invention, nucleic acid encoding the antigen may be used [e.g. refs. 151 to 159]. Protein components of the compositions of the invention may thus be replaced by nucleic acid (preferably DNA e.g. in the form of a plasmid) that encodes the protein. In practical terms, there may be an upper limit to the number of antigens included in compositions of the invention. The number of antigens in a composition of the invention may be less than 20, less than 19, less than 18, less than 17, less than 16, less than 15, less than 14, less than 13, less than 12, less than 11, less than 10, less than 9, less than 8, less than 7, less than 6, less than 5, less than 4, or less than 3. The number of antigens in a composition of the invention may be less than 6, less than 5, or less than 4.

Pharmaceutical Compositions and Methods

The invention provides processes for preparing pharmaceutical compositions, comprising the steps of mixing conjugate of the invention with a pharmaceutically acceptable carrier. Typical 'pharmaceutically acceptable carriers' include any carrier that does not itself induce the production of antibodies harmful to the individual receiving the composition. Suitable carriers are typically large, slowly metabolised macromolecules such as proteins, saccharides, polylactic acids, polyglycolic acids, polymeric amino acids, amino acid copolymers, lactose, and lipid aggregates (such as oil droplets or liposomes). Such carriers are well known to those of ordinary skill in the art. The vaccines may also contain diluents, such as water, saline, glycerol, etc. Additionally, auxiliary substances, such as wetting or emulsifying agents, pH buffering substances, and the like, may be present. Sterile pyrogen-free, phosphate-buffered physiologic saline is a typical carrier. A thorough discussion of pharmaceutically acceptable excipients is available in reference 160.

Compositions of the invention may be in aqueous form (i.e. solutions or suspensions) or in a dried form (e.g. lyophilised). If a dried vaccine is used then it will be reconstituted into a liquid medium prior to injection. Lyophilisation of conjugate vaccines is known in the art e.g. the Menjugate™ product is presented in lyophilised form, whereas NeisVac-C™ and Meningitec™ are presented in aqueous form. To stabilise conjugates during lyophilisation, it may be typical to include a sugar alcohol (e.g. mannitol) or a disaccharide (e.g. sucrose or trehalose) e.g. at between 1 mg/ml and 30 mg/ml (e.g. about 25 mg/ml) in the composition.

The pharmaceutical compositions may be packaged into vials or into syringes. The syringes may be supplied with or without needles. A syringe will include a single dose of the composition, whereas a vial may include a single dose or multiple doses.

Aqueous compositions of saccharides of the invention are suitable for reconstituting other vaccines from a lyophilised form. Where a composition of the invention is to be used for such extemporaneous reconstitution, the invention provides a process for reconstituting such a lyophilised vaccine, comprising the step of mixing the lyophilised material with an aqueous composition of the invention. The reconstituted material can be used for injection.

Compositions of the invention may be packaged in unit dose form or in multiple dose form. For multiple dose forms, vials are preferred to pre-filled syringes. Effective dosage volumes can be routinely established, but a typical human dose of the composition has a volume of 0.5 ml e.g. for intramuscular injection.

The pH of the composition is typically between 6 and 8, e.g. about 7. Stable pH may be maintained by the use of a buffer. If a composition comprises an aluminium hydroxide salt, it is typical to use a histidine buffer [161]. The composition may be sterile and/or pyrogen-free. Compositions of the invention may be isotonic with respect to humans.

Compositions of the invention are immunogenic, and are more preferably vaccine compositions. Vaccines according to the invention may either be prophylactic (i.e. to prevent infection) or therapeutic (i.e. to treat infection), but will typically be prophylactic. Immunogenic compositions used as vaccines comprise an immunologically effective amount of antigen(s), as well as any other components, as needed. By 'immunologically effective amount', it is meant that the administration of that amount to an individual, either in a single dose or as part of a series, is effective for treatment or prevention. This amount varies depending upon the health and physical condition of the individual to be treated, age, the taxonomic group of individual to be treated (e.g. non-human primate, primate, etc.), the capacity of the individual's immune system to synthesise antibodies, the degree of protection desired, the formulation of the vaccine, the treating doctor's assessment of the medical situation, and other relevant factors. It is expected that the amount will fall in a relatively broad range that can be determined through routine trials.

Within each dose, the quantity of an individual saccharide antigen will generally be between 1-50 µg (measured as mass of saccharide) e.g. about 1 µg, about 2.5 µg, about 4 µg, about 5 µg, or about 10 µg.

The compositions of the invention may be prepared in various forms. For example, the compositions may be prepared as injectables, either as liquid solutions or suspensions. The composition may be prepared for pulmonary administration e.g. as an inhaler, using a fine powder or a spray. The composition may be prepared as a suppository or pessary. The composition may be prepared for nasal, aural or ocular administration e.g. as spray, drops, gel or powder [e.g. refs 162 & 163].

Success with nasal administration of pneumococcal saccharides [164,165], Hib saccharides [166], MenC saccharides [167], and mixtures of Hib and MenC saccharide conjugates has been reported.

Compositions of the invention may include an antimicrobial, particularly when packaged in multiple dose format.

Compositions of the invention may comprise detergent e.g. a Tween (polysorbate), such as Tween 80. Detergents are generally present at low levels e.g. <0.01%.

Compositions of the invention may include sodium salts (e.g. sodium chloride) to give tonicity. A concentration of 10+2 mg/ml NaCl is typical.

Compositions of the invention will generally include a buffer. A phosphate buffer is typical.

Compositions of the invention will generally be administered in conjunction with other immunoregulatory agents. In particular, compositions will usually include one or more adjuvants. Such adjuvants include, but are not limited to:

Mineral-Containing Compositions

Mineral containing compositions suitable for use as adjuvants in the invention include mineral salts, such as aluminium salts and calcium salts. The invention includes mineral salts such as hydroxides (e.g. oxyhydroxides), phosphates (e.g. hydroxyphosphates, orthophosphates), sulphates, etc. [e.g. chapters 8 & 9 of ref. 169], or mixtures of different mineral compounds (e.g. a mixture of a phosphate and a hydroxide adjuvant, optionally with an excess of the phosphate), with the compounds taking any suitable form (e.g. gel, crystalline, amorphous, etc.), and with adsorption to the salt(s) being typical. The mineral containing compositions may also be formulated as a particle of metal salt [170].

Aluminum salts may be included in vaccines of the invention such that the dose of $Al^{3+}$ is between 0.2 and 1.0 mg per dose.

A typical aluminium phosphate adjuvant is amorphous aluminium hydroxyphosphate with $PO_4$/Al molar ratio between 0.84 and 0.92, included at 0.6 mg $Al^{3+}$/ml. Adsorption with a low dose of aluminium phosphate may be used e.g. between 50 and 100 μg $Al^{3+}$ per conjugate per dose. Where an aluminium phosphate it used and it is desired not to adsorb an antigen to the adjuvant, this is favoured by including free phosphate ions in solution (e.g. by the use of a phosphate buffer).

Oil Emulsions

Oil emulsion compositions suitable for use as adjuvants in the invention include squalene-water emulsions, such as MF59 (5% Squalene, 0.5% Tween 80, and 0.5% Span 85, formulated into submicron particles using a microfluidizer) [Chapter 10 of ref. 169; also refs. 171-173]. MF59 is used as the adjuvant in the FLUAD™ influenza virus trivalent subunit vaccine.

Particularly useful adjuvants for use in the compositions are submicron oil-in-water emulsions. Preferred submicron oil-in-water emulsions for use herein are squalene/water emulsions optionally containing varying amounts of MTP-PE, such as a submicron oil-in-water emulsion containing 4-5% w/v squalene, 0.25-1.0% w/v Tween 80 (polyoxyelthylenesorbitan monooleate), and/or 0.25-1.0% Span 85 (sorbitan trioleate), and, optionally, N-acetylmuramyl-L-alanyl-D-isogluatminyl-L-alanine-2-(1'-2'-dipalmitoyl-sn-glycero-3-hydroxyphosphophoryloxy)-ethylamine (MTP-PE). Submicron oil-in-water emulsions, methods of making the same and immunostimulating agents, such as muramyl peptides, for use in the compositions, are described in detail in references 171 & 174-175.

Complete Freund's adjuvant (CFA) and incomplete Freund's adjuvant (IFA) may also be used as adjuvants in the invention.

Saponin Formulations [Chapter 22 of Ref. 169]

Saponin formulations may also be used as adjuvants in the invention. Saponins are a heterologous group of sterol glycosides and triterpenoid glycosides that are found in the bark, leaves, stems, roots and even flowers of a wide range of plant species. Saponins isolated from the bark of the *Quillaia saponaria* Molina tree have been widely studied as adjuvants. Saponin can also be commercially obtained from *Smilax ornata* (sarsaprilla), Gypsophilla *paniculata* (brides veil), and *Saponaria officianalis* (soap root). Saponin adjuvant formulations include purified formulations, such as QS21, as well as lipid formulations, such as ISCOMs.

Saponin compositions have been purified using HPLC and RP-HPLC. Specific purified fractions using these techniques have been identified, including QS7, QS17, QS18, QS21, QH-A, QH-B and QH-C. Preferably, the saponin is QS21. A method of production of QS21 is disclosed in ref. 176. Saponin formulations may also comprise a sterol, such as cholesterol [177].

Combinations of saponins and cholesterols can be used to form unique particles called immunostimulating complexs (ISCOMs) [chapter 23 of ref. 169]. ISCOMs typically also include a phospholipid such as phosphatidylethanolamine or phosphatidylcholine. Any known saponin can be used in ISCOMs. Preferably, the ISCOM includes one or more of QuilA, QHA and QHC. ISCOMs are further described in refs. 177-179. Optionally, the ISCOMS may be devoid of additional detergent(s) [180].

A review of the development of saponin based adjuvants can be found in refs. 181 & 182.

Virosomes and Virus-Like Particles

Virosomes and virus-like particles (VLPs) can also be used as adjuvants in the invention. These structures generally contain one or more proteins from a virus optionally combined or formulated with a phospholipid. They are generally non-pathogenic, non-replicating and generally do not contain any of the native viral genome. The viral proteins may be recombinantly produced or isolated from whole viruses. These viral proteins suitable for use in virosomes or VLPs include proteins derived from influenza virus (such as HA or NA), Hepatitis B virus (such as core or capsid proteins), Hepatitis E virus, measles virus, Sindbis virus, Rotavirus, Foot-and-Mouth Disease virus, Retrovirus, Norwalk virus, human Papilloma virus, HIV, RNA-phages, Qß-phage (such as coat proteins), GA-phage, fr-phage, AP205 phage, and Ty (such as retrotransposon Ty protein p1). VLPs are discussed further in refs. 183-188. Virosomes are discussed further in, for example, ref. 189.

Bacterial or Microbial Derivatives

Adjuvants suitable for use in the invention include bacterial or microbial derivatives such as non-toxic derivatives of enterobacterial liposaccharide (LPS), Lipid A derivatives, immunostimulatory oligonucleotides and ADP-ribosylating toxins and detoxified derivatives thereof.

Non-toxic derivatives of LPS include monophosphoryl lipid A (MPL) and 3-O-deacylated MPL (3dMPL). 3dMPL is a mixture of 3 de-O-acylated monophosphoryl lipid A with 4, 5 or 6 acylated chains. A preferred "small particle" form of 3 De-O-acylated monophosphoryl lipid A is disclosed in ref. 190. Such "small particles" of 3dMPL are small enough to be sterile filtered through a 0.22 μm membrane [190]. Other non-toxic LPS derivatives include monophosphoryl lipid A mimics, such as aminoalkyl glucosaminide phosphate derivatives e.g. RC-529 [191,192].

Lipid A derivatives include derivatives of lipid A from *Escherichia coli* such as OM-174. OM-174 is described for example in refs. 193 & 194.

Immunostimulatory oligonucleotides suitable for use as adjuvants in the invention include nucleotide sequences containing a CpG motif (a dinucleotide sequence containing an unmethylated cytosine linked by a phosphate bond to a guanosine). Double-stranded RNAs and oligonucleotides containing palindromic or poly (dG) sequences have also been shown to be immunostimulatory.

The CpG's can include nucleotide modifications/analogs such as phosphorothioate modifications and can be double-stranded or single-stranded. References 195, 196 and 197 disclose possible analog substitutions e.g. replacement of guanosine with 2'-deoxy-7-deazaguanosine. The adjuvant effect of CpG oligonucleotides is further discussed in refs. 198-203.

The CpG sequence may be directed to TLR9, such as the motif GTCGTT or TTCGTT [204]. The CpG sequence may be specific for inducing a Th1 immune response, such as a CpG-A ODN, or it may be more specific for inducing a B cell response, such a CpG-B ODN. CpG-A and CpG-B ODNs are discussed in refs. 205-207. Preferably, the CpG is a CpG-A ODN.

Preferably, the CpG oligonucleotide is constructed so that the 5' end is accessible for receptor recognition. Optionally, two CpG oligonucleotide sequences may be attached at their 3' ends to form "immunomers" (e.g. refs. 204 & 208-210).

Bacterial ADP-ribosylating toxins and detoxified derivatives thereof may be used as adjuvants in the invention. Preferably, the protein is derived from *E. coli* (*E. coli* heat labile enterotoxin "LT"), cholera ("CT"), or pertussis ("PT"). The use of detoxified ADP-ribosylating toxins as mucosal adjuvants is described in ref. 211 and as parenteral adjuvants in ref. 212. The toxin or toxoid is preferably in the form of a holotoxin, comprising both A and B subunits. Preferably, the A subunit contains a detoxifying mutation; preferably the B subunit is not mutated. Preferably, the adjuvant is a detoxified LT mutant such as LT-K63, LT-R$^{72}$, and LT-G192. The use of ADP-ribosylating toxins and detoxified derivaties thereof, particularly LT-K63 and LT-R$^{72}$, as adjuvants can be found in refs. 213-220. Numerical reference for amino acid substitutions is preferably based on the alignments of the A and B subunits of ADP-ribosylating toxins set forth in ref. 221, specifically incorporated herein by reference in its entirety.

Human Immunomodulators

Human immunomodulators suitable for use as adjuvants in the invention include cytokines, such as interleukins (e.g. IL-1, IL-2, IL-4, IL-5, IL-6, IL-7, IL-12 [222], etc.) [223], interferons (e.g. interferon-γ), macrophage colony stimulating factor, and tumor necrosis factor.

Bioadhesives and Mucoadhesives

Bioadhesives and mucoadhesives may also be used as adjuvants in the invention. Suitable bioadhesives include esterified hyaluronic acid microspheres or mucoadhesives such as cross-linked derivatives of poly(acrylic acid), polyvinyl alcohol, polyvinyl pyrollidone, polysaccharides and carboxymethylcellulose. Chitosan and derivatives thereof may also be used as adjuvants in the invention [225].

Microparticles

Microparticles may also be used as adjuvants in the invention. Microparticles (i.e. a particle of ~100 nm to ~150 μm in diameter, more preferably ~200 nm to ~30 μm in diameter, and most preferably ~500 nm to ~10 μm in diameter) formed from materials that are biodegradable and non-toxic (e.g. a poly(α-hydroxy acid), a polyhydroxybutyric acid, a polyorthoester, a polyanhydride, a polycaprolactone, etc.), with poly(lactide-co-glycolide) are preferred, optionally treated to have a negatively-charged surface (e.g. with SDS) or a positively-charged surface (e.g. with a cationic detergent, such as CTAB).

Liposomes (Chapters 13 & 14 of ref. 169)

Examples of liposome formulations suitable for use as adjuvants are described in refs. 226-228.

Polyoxyethylene Ether and Polyoxyethylene Ester Formulations

Adjuvants suitable for use in the invention include polyoxyethylene ethers and polyoxyethylene esters [229]. Such formulations further include polyoxyethylene sorbitan ester surfactants in combination with an octoxynol as well as polyoxyethylene alkyl ethers or ester surfactants in combination with at least one additional non-ionic surfactant such as an octoxynol [231]. Preferred polyoxyethylene ethers are selected from the following group: polyoxyethylene-9-lauryl ether (laureth 9), polyoxyethylene-9-steoryl ether, polyoxytheylene-8-steoryl ether, polyoxyethylene-4-lauryl ether, polyoxyethylene-35-lauryl ether, and polyoxyethylene-23-lauryl ether.

Polyphosphazene (PCPP)

PCPP formulations are described, for example, in refs. 232 and 233.

Muramyl Peptides

Examples of muramyl peptides suitable for use as adjuvants in the invention include N-acetyl-muramyl-L-threonyl-D-isoglutamine (thr-MDP), N-acetyl-normuramyl-L-alanyl-D-isoglutamine (nor-MDP), and N-acetylmuramyl-L-alanyl-D-isoglutaminyl-L-alanine-2-(1'-2'-dipalmitoyl-sn-glycero-3-hydroxyphosphoryloxy)-ethylamine MTP-PE).

Imidazoquinolone Compounds.

Examples of imidazoquinolone compounds suitable for use adjuvants in the invention include Imiquamod and its homologues (e.g. "Resiquimod 3M"), described further in refs. 234 and 235.

Thiosemicarbazone Compounds.

Examples of thiosemicarbazone compounds, as well as methods of formulating, manufacturing, and screening for compounds all suitable for use as adjuvants in the invention include those described in ref. 236. The thiosemicarbazones are particularly effective in the stimulation of human peripheral blood mononuclear cells for the production of cytokines, such as TNF-α.

Tryptanthrin Compounds.

Examples of tryptanthrin compounds, as well as methods of formulating, manufacturing, and screening for compounds all suitable for use as adjuvants in the invention include those described in ref. 237. The tryptanthrin compounds are particularly effective in the stimulation of human peripheral blood mononuclear cells for the production of cytokines, such as TNF-α.

The invention may also comprise combinations of aspects of one or more of the adjuvants identified above. For example, the following combinations may be used as adjuvant compositions in the invention: (1) a saponin and an oil-in-water emulsion [238]; (2) a saponin (e.g. QS21)+a non-toxic LPS derivative (e.g. 3dMPL) [239]; (3) a saponin (e.g. QS21)+a non-toxic LPS derivative (e.g. 3dMPL)+a cholesterol; (4) a saponin (e.g. QS21)+3dMPL+IL-12 (optionally+a sterol) [240]; (5) combinations of 3dMPL with, for example, QS21 and/or oil-in-water emulsions [241]; (6) SAF, containing 10% squalane, 0.4% Tween 80™, 5% pluronic-block polymer L$^{121}$, and thr-MDP, either microfluidized into a submicron emulsion or vortexed to generate a larger particle size emulsion. (7) Ribi™ adjuvant system (RAS), (Ribi Immunochem) containing 2% squalene, 0.2% Tween 80, and one or more bacterial cell wall components from the group consisting of monophosphorylipid A (MPL), trehalose dimycolate (TDM), and cell wall skeleton (CWS), preferably MPL+CWS (Detox™); and (8) one or more mineral salts (such as an aluminum salt)+a non-toxic derivative of LPS (such as 3dMPL).

Other substances that act as immunostimulating agents are disclosed in chapter 7 of ref. 169.

The use of aluminium salt adjuvants is particularly useful, and antigens are generally adsorbed to such salts. The Menjugate™ and NeisVac™ conjugates use a hydroxide adjuvant, whereas Meningitec™ uses a phosphate adjuvant. It is possible in compositions of the invention to adsorb some antigens to an aluminium hydroxide but to have other antigens in association with an aluminium phosphate. Typically, however, only a single salt is used, e.g. a hydroxide or a phosphate, but not both. Not all conjugates need to be adsorbed i.e. some or all can be free in solution.

Methods of Treatment

The invention also provides a method for raising an immune response in a mammal, comprising administering a pharmaceutical composition of the invention to the mammal. The immune response is preferably protective and preferably involves antibodies. The method may raise a booster response.

The mammal is preferably a human. Where the vaccine is for prophylactic use, the human is preferably a child (e.g. a toddler or infant) or a teenager; where the vaccine is for therapeutic use, the human is preferably an adult. A vaccine intended for children may also be administered to adults e.g. to assess safety, dosage, immunogenicity, etc. A preferred class of humans for treatment are patients at risk of nosocomial infection, particularly those with end-stage renal disease and/or on haemodialysis. Other patients at risk of nosocomial infection are also preferred, e.g. immunodeficient patients or those who have undergone surgery, especially cardiac surgery, or trauma. Another preferred class of humans for treatment are patients at risk of bacteremia.

The invention also provides a composition of the invention for use as a medicament. The medicament is preferably able to raise an immune response in a mammal (i.e. it is an immunogenic composition) and is more preferably a vaccine.

The invention also provides the use of a conjugate of the invention in the manufacture of a medicament for raising an immune response in a mammal.

These uses and methods are preferably for the prevention and/or treatment of a disease caused by S. agalactiae e.g. neonatal sepsis or bacteremia, neonatal pneumonia, neonatal meningitis, endometritis, osteomyelitis, septic arthritis, etc.

The subject in which disease is prevented may not be the same as the subject that receives the conjugate of the invention. For instance, a conjugate may be administered to a female (before or during pregnancy) in order to protect offspring (so-called 'maternal immunisation' [242-244]).

One way of checking efficacy of therapeutic treatment involves monitoring GBS infection after administration of the composition of the invention. One way of checking efficacy of prophylactic treatment involves monitoring immune responses against the GBS antigens after administration of the composition.

Preferred compositions of the invention can confer an antibody titre in a patient that is superior to the criterion for seroprotection for each antigenic component for an acceptable percentage of human subjects. Antigens with an associated antibody titre above which a host is considered to be seroconverted against the antigen are well known, and such titres are published by organisations such as WHO. Preferably more than 80% of a statistically significant sample of subjects is seroconverted, more preferably more than 90%, still more preferably more than 93% and most preferably 96-100%. Compositions of the invention will generally be administered directly to a patient. Direct delivery may be accomplished by parenteral injection (e.g. subcutaneously, intraperitoneally, intravenously, intramuscularly, or to the interstitial space of a tissue), or by rectal, oral, vaginal, topical, transdermal, intranasal, ocular, aural, pulmonary or other mucosal administration. Intramuscular administration to the thigh or the upper arm is preferred. Injection may be via a needle (e.g. a hypodermic needle), but needle-free injection may alternatively be used. A typical intramuscular dose is 0.5 ml.

The invention may be used to elicit systemic and/or mucosal immunity.

Dosage treatment can be a single dose schedule or a multiple dose schedule. Multiple doses may be used in a primary immunisation schedule and/or in a booster immunisation schedule. A primary dose schedule may be followed by a booster dose schedule. Suitable timing between priming doses (e.g. between 4-16 weeks), and between priming and boosting, can be routinely determined.

General

The practice of the present invention will employ, unless otherwise indicated, conventional methods of chemistry, biochemistry, molecular biology, immunology and pharmacology, within the skill of the art. Such techniques are explained fully in the literature (e.g., refs. 245-252, etc.).

The term "comprising" encompasses "including" as well as "consisting" e.g. a composition "comprising" X may consist exclusively of X or may include something additional e.g. X+Y. In some implementations, the term "comprising" refers to the inclusion of the indicated active agent, such as recited polypeptides, as well as inclusion of other active agents, and pharmaceutically acceptable carriers, excipients, emollients, stabilizers, etc., as are known in the pharmaceutical industry. In some implementations, the term "consisting essentially of" refers to a composition, whose only active ingredient is the indicated active ingredient(s), however, other compounds may be included which are for stabilizing, preserving, etc. the formulation, but are not involved directly in the therapeutic effect of the indicated active ingredient. Use of the transitional phrase "consisting essentially" means that the scope of a claim is to be interpreted to encompass the specified materials or steps recited in the claim, and those that do not materially affect the basic and novel characteristic(s) of the claimed invention. See, In re Herz, 537 F.2d 549, 551-52, 190 USPQ 461, 463 (CCPA 1976); see also MPEP § 2111.03. Thus, the term "consisting essentially of" when used in a claim of this invention is not intended to be interpreted to be equivalent to "comprising".

The term "about" in relation to a numerical value x means, for example, x±10%.

The word "substantially" does not exclude "completely" e.g. a composition which is "substantially free" from Y may be completely free from Y. Where necessary, the word "substantially" may be omitted from the definition of the invention.

Where the invention provides a process involving multiple sequential steps, the invention can also provide a process involving less than the total number of steps. The different steps can be performed at very different times by different people in different places (e.g. in different countries).

It will be appreciated that sugar rings can exist in open and closed form and that, whilst closed forms are shown in structural formulae herein, open forms are also encompassed by the invention. Similarly, it will be appreciated that sugars can exist in pyranose and furanose forms and that, whilst pyranose forms are shown in structural formulae herein, furanose forms are also encompassed. Different anomeric forms of sugars are also encompassed.

MODES FOR CARRYING OUT THE INVENTION

A. Saccharide Derivatization

GBS serotype II and V saccharides were reacted with $NaIO_4$ to effect oxidation of sialic acid residues to aldehyde groups. The extent of oxidation of the sialyl moieties was controlled by varying the amount of $NaIO_4$ used. Reductive amination of the aldehydes provided amine groups for the insertion of different spacers, facilitating attachment of the cyclooctyne group to the saccharides. Various cyclooctyne-containing compounds were tested to establish the optimal length for the spacer, as shown in FIG. 1.

Figure 2:
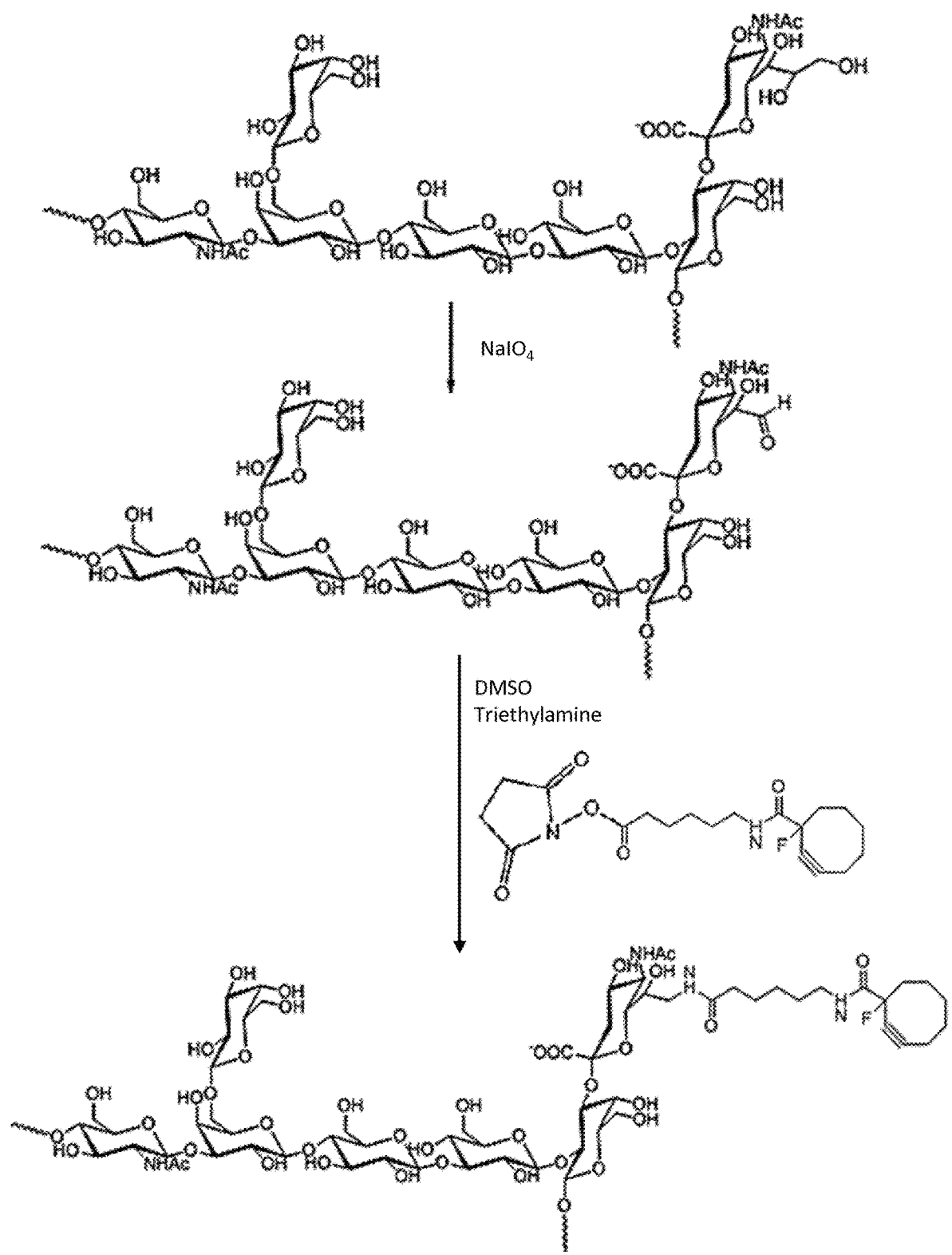
FIG. 2 shows a general reaction scheme for the attachment of a cyclooctyne group to a GBS serotype II saccharide.

Reactions were monitored by NMR spectroscopy and carbohydrate recoveries were quantified using colorimetric determination of sialic acid. FIG. 2 shows a general reaction scheme for the attachment of a cyclooctyne group to a GBS serotype II saccharide.

Figure 3:
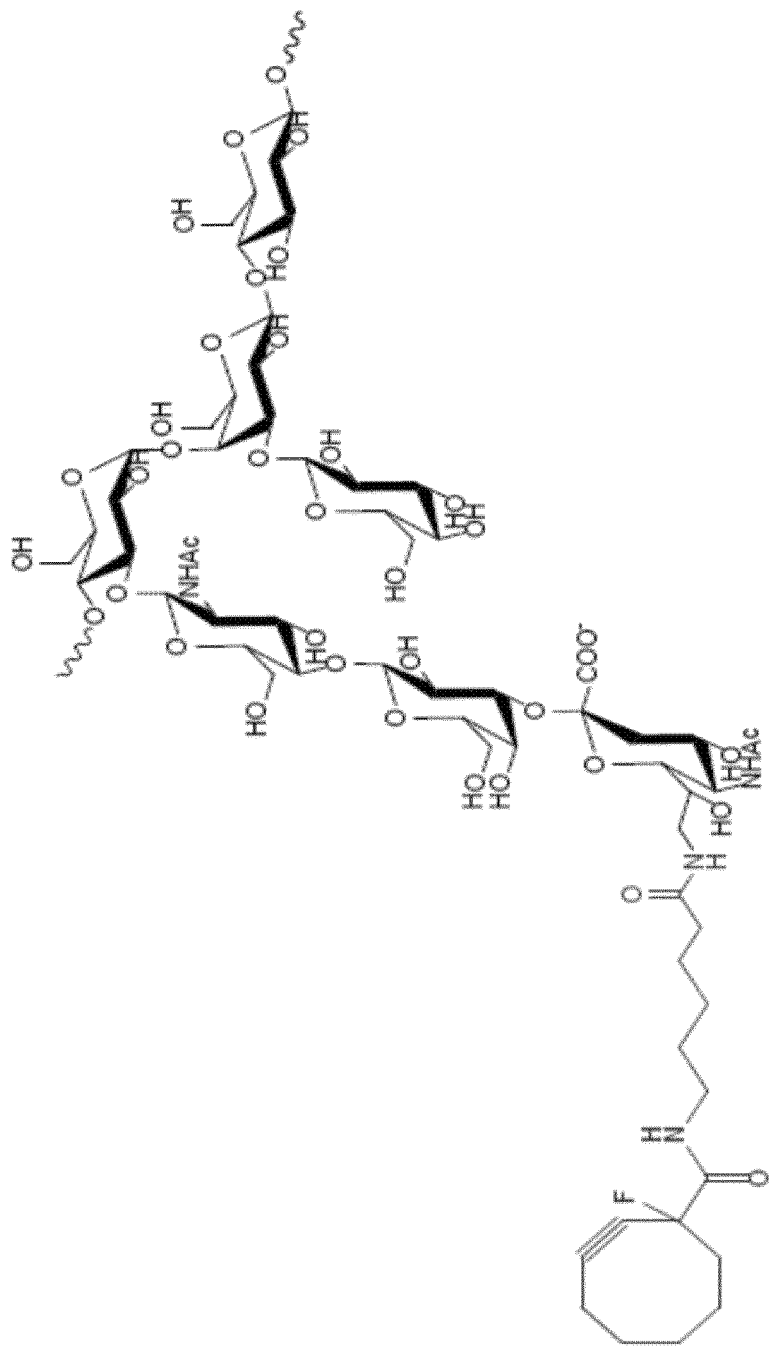
FIG. 3 shows the structure of GBS serotype V saccharide with cyclooctyne group attached (I).
Figure 4:
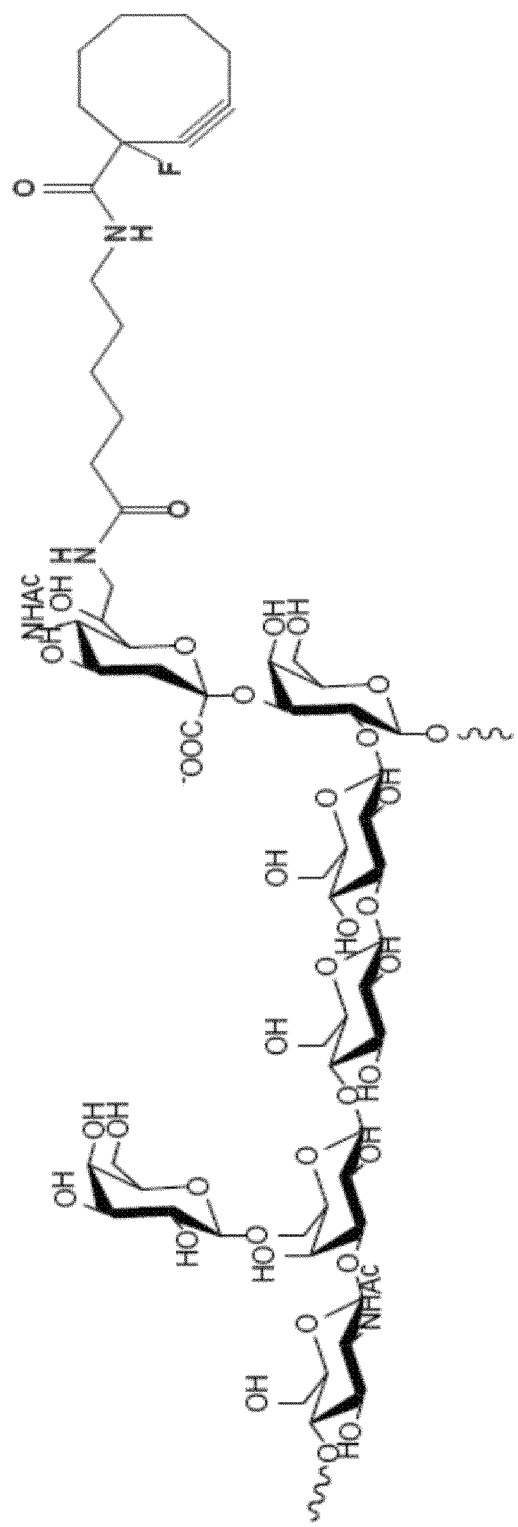
FIG. 4 shows the structure of GBS serotype II saccharide with cyclooctyne group attached (II).

Using this method, two saccharide derivatives were produced, as shown in FIG. 3 (GBS serotype V saccharide with cyclooctyne group attached (I)) and FIG. 4 (GBS serotype II saccharide with cyclooctyne group attached (II)).

The amount of each reactant used in the synthesis of GBS serotype V saccharide with cyclooctyne group attached (I) was as follows:

| Compound | MW | mg | mmol NH$_2$ | eq | ml |
|---|---|---|---|---|---|
| GBS serotype V saccharide-NH$_2$ | 1323 | 30 | 0.00453 | | |
| Cyclooctyne-N-hydroxysuccinimide ester spacer | 380 | 13 | | 10 | |
| Triethylamine | | | | | 0.05 |
| DMSO | | | | | 3 |

The amount of each reactant used in the synthesis of GBS serotype II saccharide with cyclooctyne group attached (II) was as follows:

| Compound | MW | mg | mmol NH$_2$ | eq | ml |
|---|---|---|---|---|---|
| GBS serotype II saccharide-NH$_2$ | 1323 | 40 | 0.00393 | | |
| Cyclooctyne-N-hydroxysuccinimide ester spacer | 380 | 13 | | 10 | |
| Triethylamine | | | | | 0.04 |
| DMSO | | | | | 3 |

Figure 10:
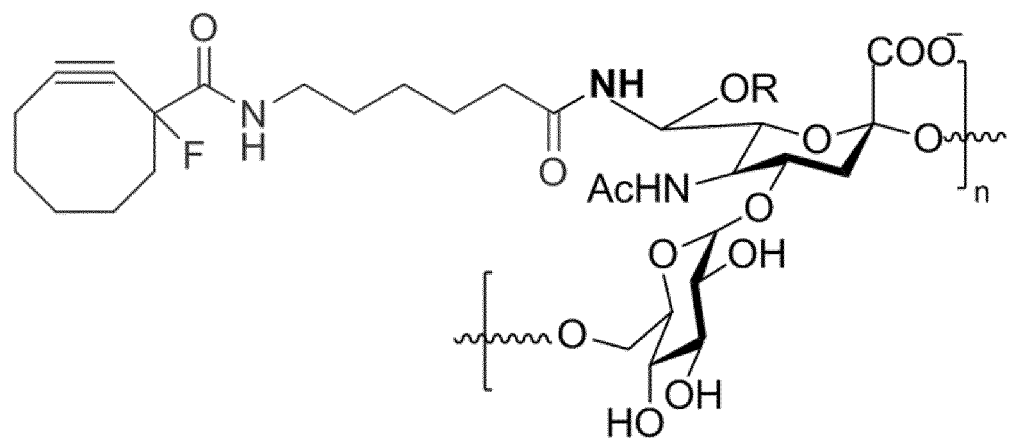
FIG. 10 shows the structure of MenY saccharide with cyclooctyne group attached (III).

A further saccharide derivative was produced as shown in FIG. 10 (MenY saccharide with cyclooctyne group attached (III)).

Saccharide derivatives were also synthesized using the other two cycloalkyne systems shown in FIG. 1.

B. Production and Purification of Conjugates

Figure 5:
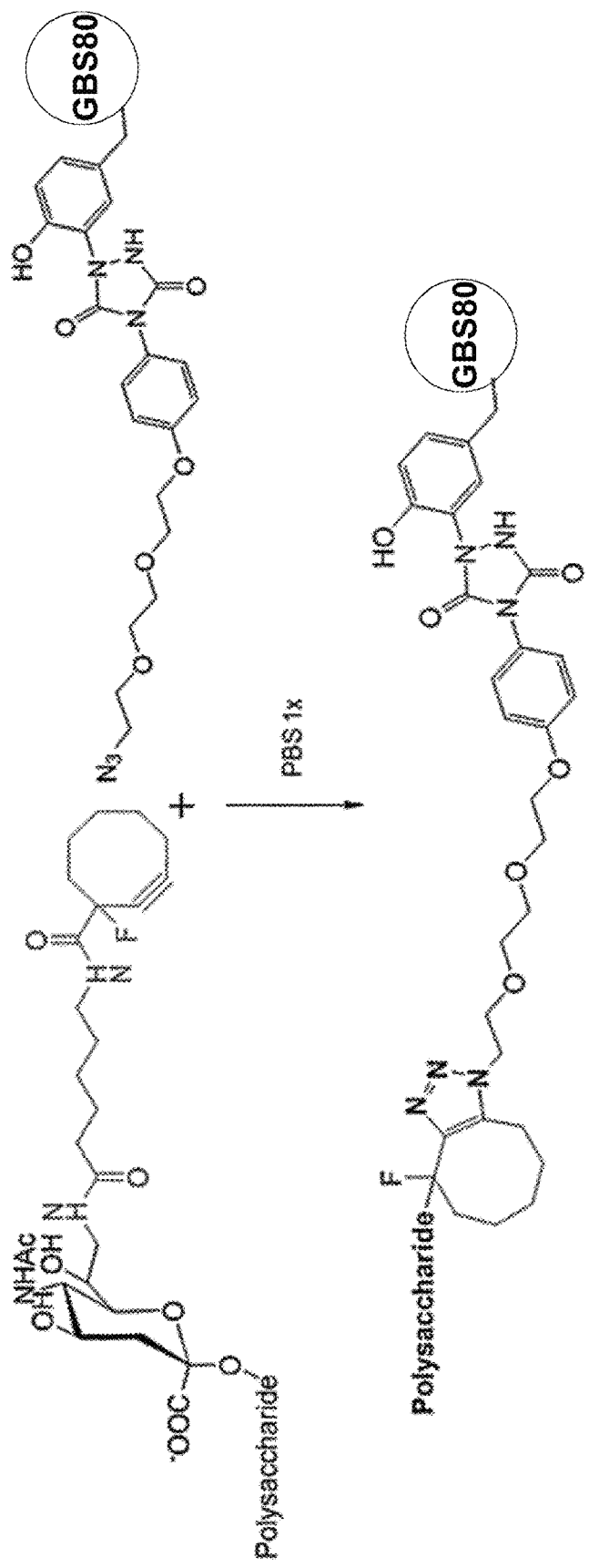
FIG. 5 shows a general reaction scheme for the conjugation of saccharide derivative (II) to a GBS80 carrier protein via a tyrosine residue.
Figure 7:
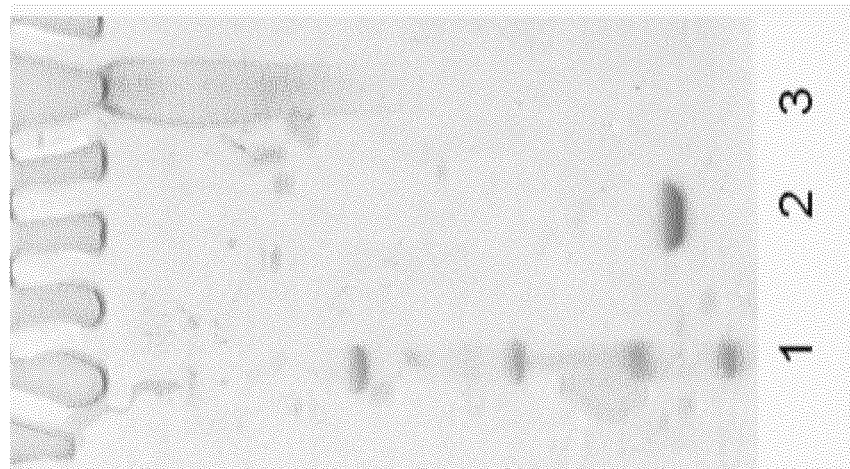
FIG. 7 shows the results of SDS-PAGE characterization for conjugate B (1=MW, 2=GBS80-Y-$N_3$, 3=GBS80-Y-$N_3$/PSII after purification).
Figure 6:
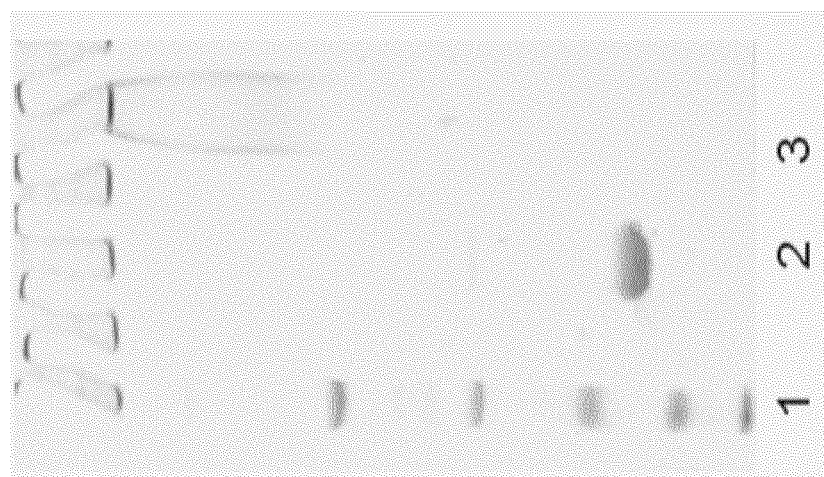
FIG. 6 shows the results of SDS-PAGE characterization for conjugate A (1=MW, 2=GBS80-Y-$N_3$, 3=GBS80-Y-$N_3$/PSV after purification).
Figure 9:
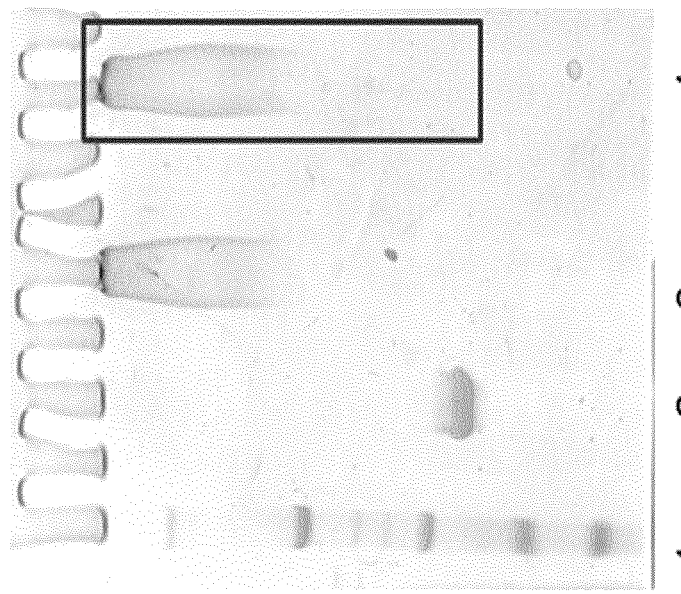
FIG. 9 shows the results of SDS-PAGE characterization for conjugate D (1=MW, 2-GBS67-Y-N$_3$, 3=GBS67-Y-N$_3$/PSII after purification, 4=GBS67-Y-N$_3$/PSII after purification).
Figure 8:
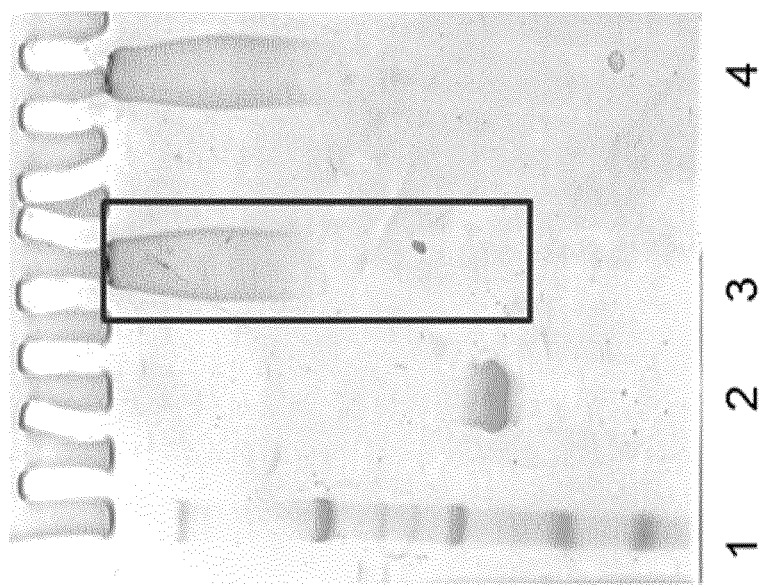
FIG. 8 shows the results of SDS-PAGE characterization for conjugate C (1=MW, 2=GBS67-Y-$N_3$, 3=GBS67-Y-$N_3$/PSII after purification, 4=GBS67-Y-$N_3$/PSII after purification).

Spacers enabling conjugation of the protein (GBS60 or GBS67) were installed by site directed Mannich-type reaction onto tyrosine using the procedures described in PCT/US2012/045549, yielding carrier protein attached to a terminal azide group. Carrier protein-azide was reacted with the saccharide-cyclooctyne to effect an azide-alkyne cycloaddition reaction, yielding carrier protein-saccharide conjugate. FIG. 5 shows a general reaction scheme for the conjugation of saccharide derivative (II) to a GBS80 carrier protein via a tyrosine residue.

Eight different conjugates containing GBS protein were synthesised, as follows (where "Y" denotes attachment to carrier protein GBS80 or GBS67 via a tyrosine residue and "N$_3$" denotes the triazole linkage):

A. GBS80-Y-N$_3$-GBS serotype V saccharide
B. GBS80-Y-N$_3$-GBS serotype II saccharide
C. GBS67-Y-N$_3$-GBS serotype II saccharide
D. GBS67-Y-N$_3$-GBS serotype V saccharide Conjugation was carried out at a saccharide: protein ratio of 6:1 (w/w) for conjugates A-B and at a saccharide: protein ration of 4:1 (w/w) for conjugates C-D. Addition of protein (in PBS) at a concentration of 5 mg/ml to saccharide followed by stirring at room temperature for 6-12 hours yielded conjugates. Conjugates were purified using a hydroxyapatite column to remove free protein (with a 2 mM NaPi, pH 7.2 mobile phase buffer followed by a 400 mM NaPi, pH 7.2 mobile phase buffer) and free saccharide (with a 2 mM NaPi, 550 mM NaCl, pH 7.2 mobile phase buffer followed by a 10 mM NaPi, pH 7.2 mobile phase buffer followed by a 35 mM NaPi, pH 7.2 mobile phase buffer followed by a 400 mM NaPi, pH 7.2 mobile phase buffer).

SDS-PAGE (3-8%) was used to confirm formation of the conjugates. The results of the SDS-PAGE characterization for each of conjugates A-D are shown in FIGS. 6-9, respectively.

HPAEC-PAD analysis was used to determine the saccharide content of the conjugates. The conjugates had the following properties:

| Conjugate | Protein | Saccharide/ protein (w/w) | Free saccharide (%) | Total protein (mg) | Saccharide/ protein used for conjugation (w/w) | Yield (% final protein) |
|---|---|---|---|---|---|---|
| A | GBS80 | 2.2 | <5.5 | 648.0 | 6:1 | 21.1 |
| B | GBS80 | 2.7 | <1.8 | 810.0 | 6:1 | 52.5 |
| C | GBS67 | 1.1 | <4.5 | 975.0 | 4:1 | 29.5 |
| D | GBS67 | 2.5 | <4.8 | 780.0 | 4:1 | 23.6 |

A conjugate containing CRM197 protein was also synthesised. In particular, saccharide derivative (III) was conjugated to CRM197 protein, as follows:

E. CRM197-Y-N3-MenY Saccharide

Figure 11:
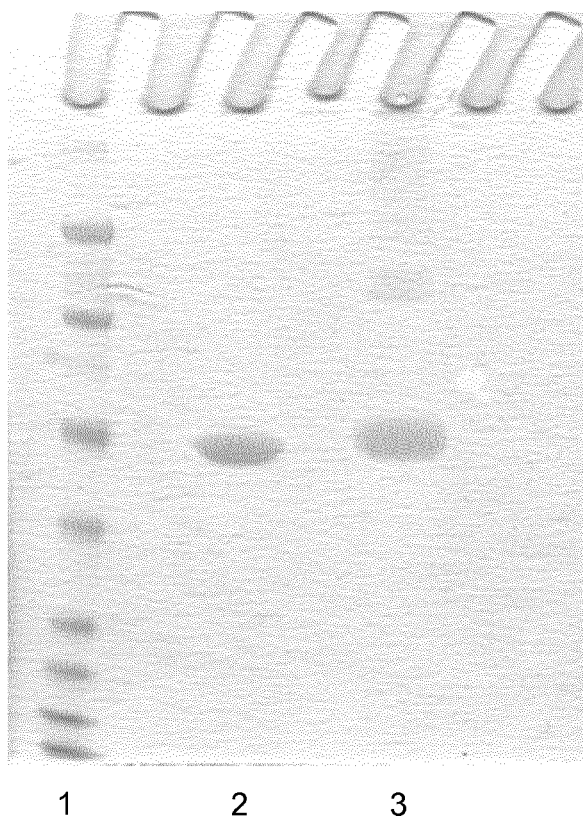
FIG. 11 shows the results of SDS-PAGE characterization for conjugate E (1=MW, 2=CRM$_{197}$-Y-N$_3$, 3=CRM$_{197}$-Y-N$_3$/MenY).

Conjugation was carried out using 60 equivalents of saccharide derivative (2.1 mg) and 1.5 mg of protein. SDS-PAGE was used to confirm formation of the conjugate. The results of the SDS-PAGE characterization for conjugate E are shown in FIG. 11.

C. Immunization Studies Using the Conjugates

The immunogenicity of various antigens was tested in mice as outlined below.

Challenge Model Using Type V Strain

Groups of eight CDI mice were immunised by intraperitoneal injection with a 1.0 μg dose of saccharide in an injection volume of 200 μl with AlumOH as adjuvant. Injections were carried out at 1, 21 and 35 days, with bleeding performed at 1, 35 and 49 days. Immunisations were carried out in groups of eight mice with the following antigens: (i) PBS, (ii) CRM197-GBS serotype V saccharide, (iii) TT-GBS serotype V saccharide, (iv) GBS80-GBS serotype V saccharide and (v) GBS80-Y-N$_3$-GBS serotype V saccharide (conjugate A). Conjugates (i) to (iv) were prepared using classical conjugation methodologies (e.g. as disclosed in reference [253]), whereas conjugate (v) was prepared using click chemistry. The neonates were challenged with type V strains. Results are shown below:

| Antigen | Protection/ treated | % Protection |
|---|---|---|
| PBS | 19/40 | 47 |
| CRM197-GBS serotype V saccharide | 61/70 | 87 |
| TT-GBS serotype V saccharide | — | — |
| GBS80-GBS serotype V saccharide | 54/57 | 95 |
| GBS80-Y-N$_3$-GBS serotype V saccharide A | 23/70 | 33 |

Challenge Model Using Type II Strain

Groups of eight CDI mice were immunised by intraperitoneal injection with a 1.0 μg dose of saccharide in an injection volume of 200 μl with AlumOH as adjuvant. Injections were carried out at 1, 21 and 35 days, with bleeding performed at 1, 35 and 49 days. Immunisations were carried out in groups of eight mice with the following antigens: (i) PBS, (ii) CRM197-GBS serotype II saccharide, (iii) TT-GBS serotype II saccharide, (iv) GBS80-GBS serotype II saccharide and (v) GBS80-Y-N$_3$-GBS serotype II saccharide (conjugate B). Conjugates (i) to (iv) were prepared using classical conjugation methodologies, whereas conjugate (v) was prepared using click chemistry. The neonates were challenged with type II strains. Results are shown below:

| Antigen | Protection/ treated | % Protection |
|---|---|---|
| PBS | 18/60 | 30 |
| CRM197-GBS serotype II saccharide | 32/50 | 64 |
| TT-GBS serotype II saccharide | 19/30 | 63 |
| GBS80-GBS serotype II saccharide | 37/70 | 53 |
| GBS80-Y-$N_3$-GBS serotype II saccharide B | 58/65 | 89 |

These results show that higher levels of protection were achieved with GBS80-Y-$N_3$-GBS serotype II saccharide B than with the CRM197 and GBS80 conjugates obtained using classical conjugation methods.

ELISA Immunoassay for Determining IgG Titers Against GBS Serotype II Saccharide Antigens IgG titers against GBS serotype II saccharide in the sera from immunized animals were measured as follows. Microtiter plates were coated with antigens (e.g. GBS80-Y-$N_3$-GBS serotype II saccharide B) and the plates were incubated overnight at room temperature and then washed three times in washing buffer (0.05% Tween 20 in PBS). After dispensing 250 μl of PBS, 2% BSA, 0.05% Tween 20 per well, plates were incubated 90 minutes at 37° C. and then aspirated to remove the post-coating solution. Test sera were diluted 1:400 in PBS, 2% BSA, 0.05% Tween 20. Standard serum was prepared by pooling hyper immune sera and initial dilutions of standard pools were chosen to obtain an optical density (OD) of about 2.000 at 405 nm. The plates were incubated for 1 hour at 37° C. and then washed with washing buffer and 100 μL of Alkaline Phosphatase-Conjugated antimouse IgG 1:1000 in dilution buffer were dispensed in each well. The plates were incubated 90 minutes at 37° C. and then washed with washing buffer. 100 μL of a solution of p-NitroPhenylPhosphate (p-NPP) 4.0 mg/mL in substrate buffer were dispensed in each well. The plates were incubated 30 minutes at room temperature and then 100 μL of a solution of EDTA 7% (w/v) disodium salt plus $Na_2HPO_4$ 3.5% pH 8.0, were added to each well to stop the enzymatic reaction. The optical density (OD) at 405 nm was measured. Total IgG titres against GBS serotype II saccharide antigen were calculated by using the Reference Line Assay Method and results were expressed as arbitrary ELISA Units/mL (EU/mL). For each of the three antigens, the standard serum IgG titer was arbitrarily assigned a value of 1.0 EU/mL. The IgG titer of each serum was estimated by interpolating the obtained ODs with the titration curve (bias and slope) of the standard pool.

Figure 12:
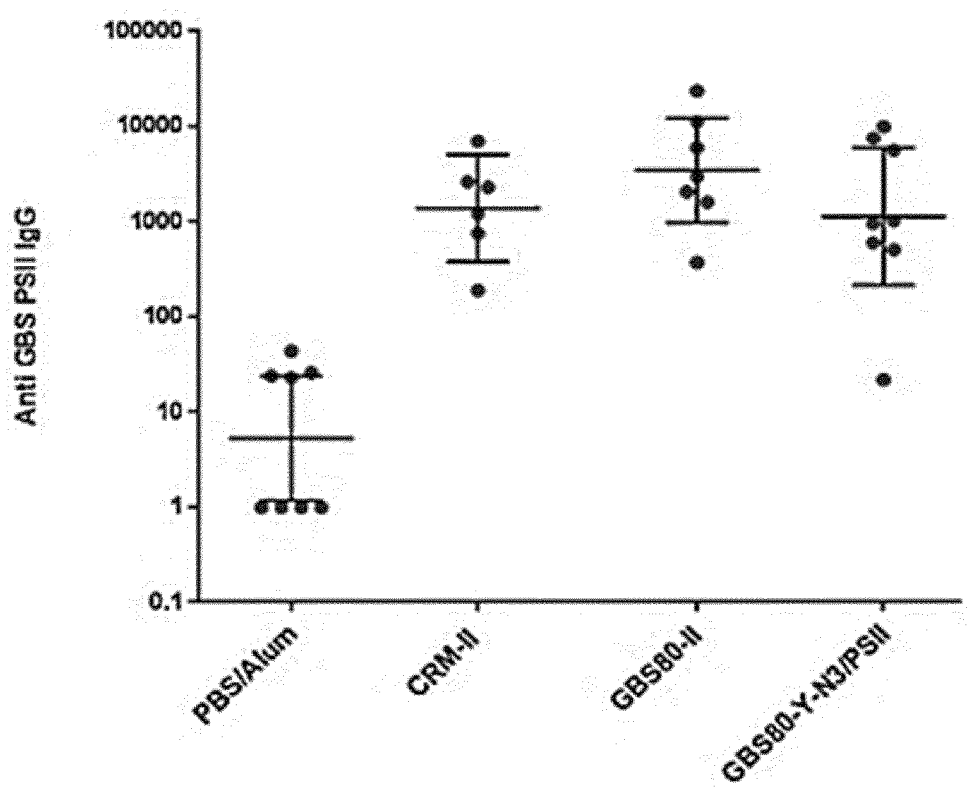
FIG. 12 shows ELISA immunoassay results for determination of IgG titers against GBS serotype II saccharide antigens (for 1.0 µg carbohydrate dose).
Figure 13:
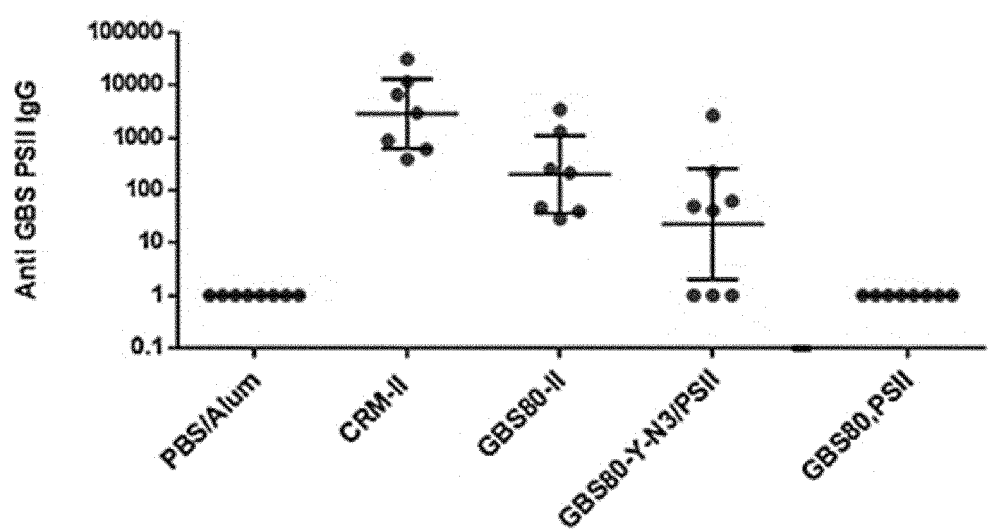
FIG. 13 shows ELISA immunoassay results for determination of IgG titers against GBS serotype II saccharide antigens (for 0.5 µg carbohydrate dose).
Figure 14:
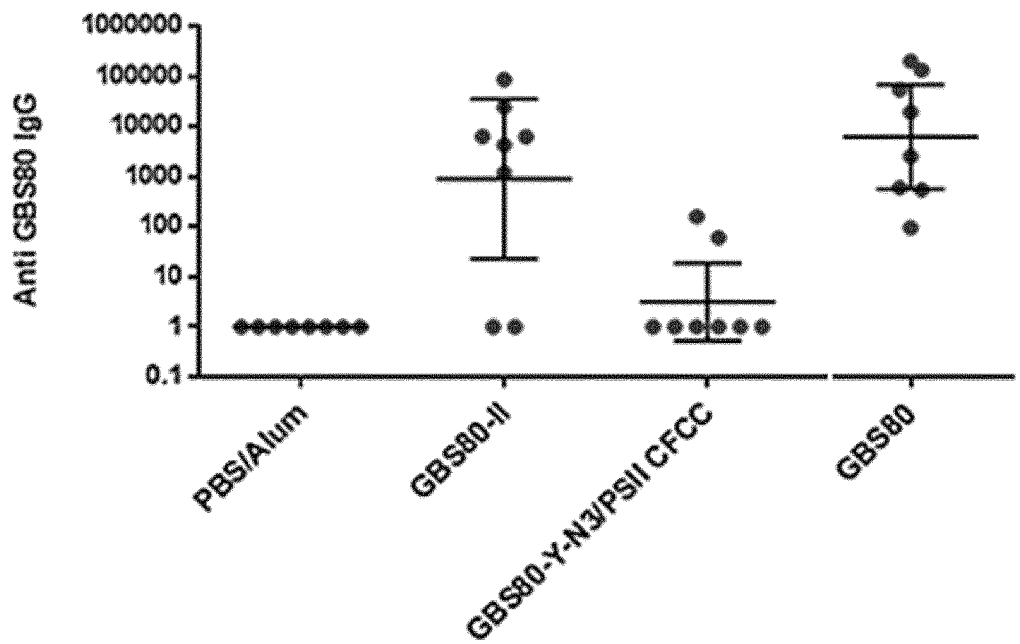
FIG. 14 shows ELISA immunoassay results for determination of IgG titers against GBS serotype II saccharide antigens (for 1.0 µg protein dose).

The results are displayed in FIG. 12 (for 1.0 μg carbohydrate dose), FIG. 13 (for 0.5 μg carbohydrate dose) and FIG. 14 (for 1.0 μg protein dose). At 1.0 μg carbohydrate dose GBS80-Y-$N_3$-GBS serotype II saccharide B IgG titers are not statistically different from the CRM197 and GBS80 conjugates obtained using classical conjugation methods. At 0.5 μg carbohydrate dose GBS80-Y-$N_3$-GBS serotype II saccharide B IgG titers are not statistically different from all the new conjugates and control.

Opsonophagocytosis Assay

Figure 15:
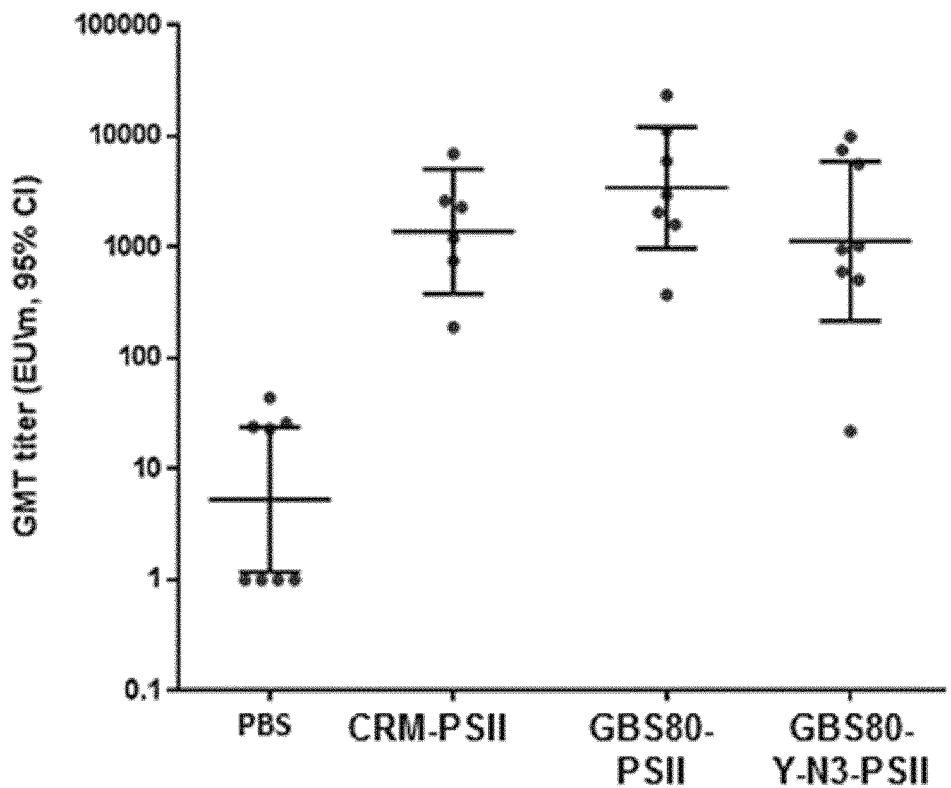
FIG. 15 shows opsonophagocytosis assay results using GBS strains.

The opsonophagocytosis assay was performed using GBS strains as target cells and HL-60 cell line (ATCC; CCL-240), differentiated into granulocyte-like cells, by adding 100 mM N,N dimethylformamide (Sigma) to the growth medium for 4 days. Mid-exponential bacterial cells were incubated at 37° C. for 1 h in the presence of phagocytic cells, 10% baby rabbit complement (Cedarlane), and heat-inactivated mouse antisera. Negative controls consisted of reactions either with preimmune sera, or without HL-60, or with heat-inactivated complement. The amount of opsonophagocytic killing was determined by subtracting the log of the number of colonies surviving the 1-h assay from the log of the number of CFU at the zero time point. Results of the experiments are shown in FIG. 15 and below:

| Antigen | OPKA titer |
|---|---|
| PBS | 10 |
| CRM197-GBS serotype II saccharide | 2306 |
| GBS80-GBS serotype II saccharide | 2443 |
| GBS80-Y-$N_3$-GBS serotype II saccharide B | 1415 |

GBS80-Y-$N_3$-GBS serotype II saccharide B OPKA and IgG titers are statistically comparable to the CRM197 and GBS80 conjugates obtained using classical conjugation methods. OPKA and IgG titers show good correlation with % of survival in challenge animal model.

Immunogenicity of Conjugates Prepared at Different Saccharide: Protein Ratios

Figure 16:
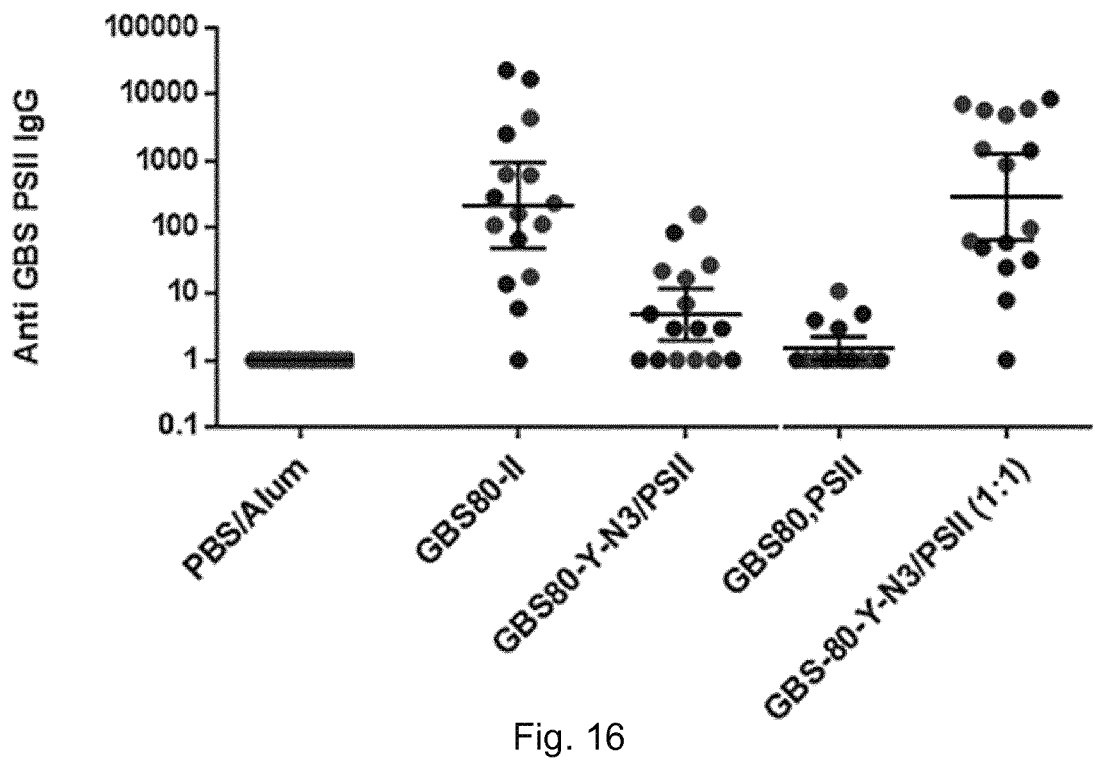
FIG. 16 shows immune response of various antigens against GBS serotype II saccharide.

Immune response was assessed against GBS serotype II saccharide (with 1.0 μg protein dose) with conjugates having different saccharide: protein ratios. The results are shown in FIG. 16 and below:

| Antigen | PS/ protein ratio (w/w) | Protection/ treated (challenge strain DK21) | % Protection |
|---|---|---|---|
| PBS | | 6/59 | 10 |
| GBS80, GBS serotype II saccharide | | 42/79 | 53 |
| GBS80-GBS serotype II saccharide | 1.8 | 36/60 | 60 |
| GBS80-Y-$N_3$-GBS serotype II saccharide | 2.7 | 32/80 | 40 |
| GBS80-Y-$N_3$-GBS serotype II saccharide | 1.1 | 68/69 | 98 |

Figure 17:
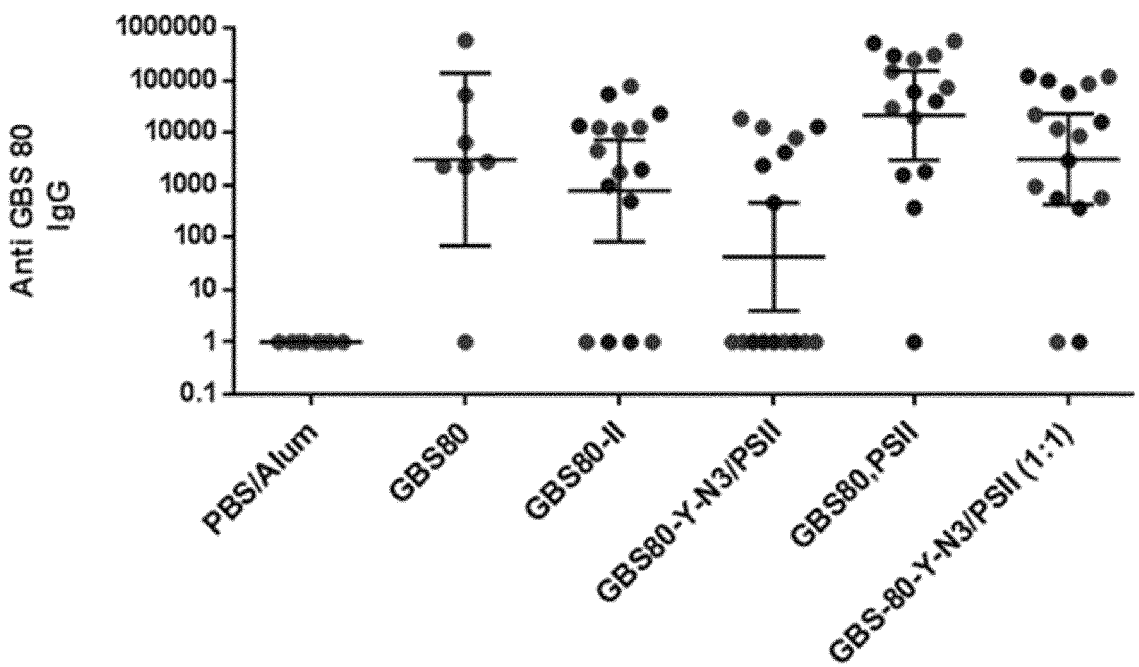
FIG. 17 shows immune response of various antigens against GBS80.

Immune response was also assessed against GBS80 (with 1.0 μg protein dose) with conjugates having different saccharide: protein ratios. The results are shown in FIG. 17 and below:

| Antigen | PS/ protein ratio (w/w) | Protection/ treated (challenge strain COH1) | % Protection |
|---|---|---|---|
| PBS | | 28/80 | 35 |
| GBS80 | | 35/60 | 58 |
| GBS80, GBS serotype II saccharide | | 37/50 | 74 |
| GBS80-GBS serotype II saccharide | 1.8 | 30/60 | 50 |
| GBS80-Y-$N_3$-GBS serotype II saccharide | 2.7 | 36/80 | 45 |
| GBS80-Y-$N_3$-GBS serotype II saccharide | 1.1 | 49/70 | 70 |

Assessment of Presence of Anti-Linker Antibodies

Figure 18:
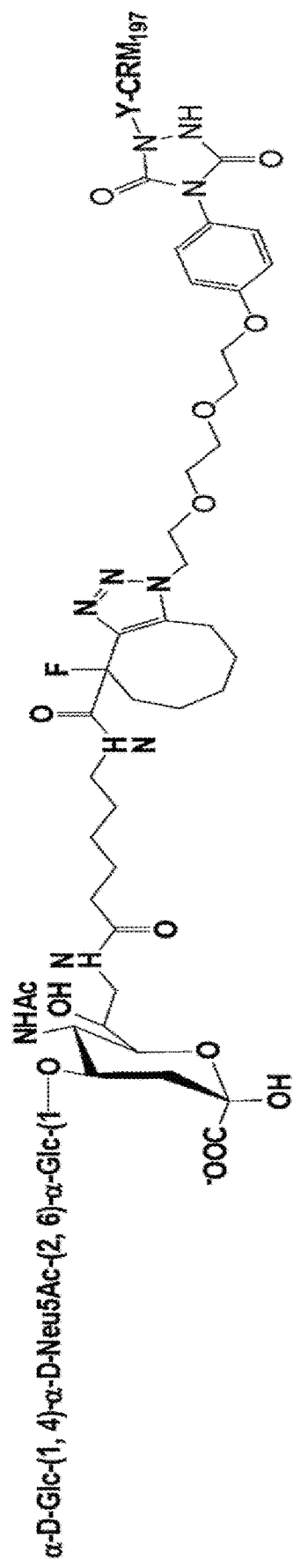
FIG. 18 shows the structure of a construct prepared via tyrosine selective conjugation of a MenY dimer to CRM197.

A construct was prepared via tyrosine selective conjugation of a MenY dimer to CRM197 (FIG. 18). Low levels of antibodies directed to the linker were found.

It will be understood that the invention has been described by way of example only and modifications may be made whilst remaining within the scope and spirit of the invention.

EMBODIMENTS

The invention includes the following numbered embodiments:

1. A method of derivatizing a saccharide comprising attaching an eight-membered cycloalkyne group to the saccharide.

2. The method of embodiment 1, wherein the eight-membered cycloalkyne group is fused to a cyclopropane group.

3. The method of embodiment 1, wherein the eight-membered cycloalkyne group is fused to two benzene groups.

4. The method of embodiment 1, wherein the eight-membered cycloalkyne group is a cyclooctyne group.

5. The method of any preceding embodiment, wherein the saccharide is a capsular saccharide.

6. The method of any preceding embodiment, wherein the saccharide is a GBS capsular saccharide.

7. The method of any preceding embodiment, wherein the saccharide is a GBS saccharide from serotype Ia, Ib, II, III or V.

8. The method of any preceding embodiment, wherein the saccharide is a GBS saccharide from serotype II or V.

9. The method of any preceding embodiment, wherein the eight-membered cycloalkyne group is attached to the saccharide via a spacer.

10. The method of embodiment 9, wherein the eight-membered cycloalkyne group is on a terminus of the spacer.

11. The method of embodiment 10, wherein the other terminus of the spacer has a functional group for attachment to the saccharide.

12. The method of embodiment 11, wherein the attachment is carried out using a compound having the formula $X_1$-L-$X_2$, where $X_1$ is the eight-membered cycloalkyne group and $X_2$-L is the spacer in which $X_2$ is any group that can react with a functional group on the saccharide and L is a linking moiety in the spacer.

13. The method of embodiment 12, wherein $X_2$ is N-oxysuccinimide.

14. The method of embodiment 12 or 13, wherein L has the formula -$L^3$-$L^2$-$L^1$-, wherein $L^1$ is carbonyl, $L^2$ is a straight chain alkyl with 1 to 10 carbon atoms or $L^2$ is absent, and $L^3$ is —NHC(O)—, carbonyl or —O(CH$_3$)—.

15. The method of any one of embodiments 12 to 14, wherein the compound having the formula $X_1$-L-$X_2$ is:

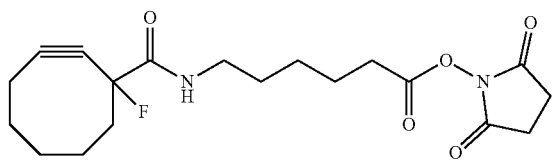 [SMILES: O=C(CCCCCNC(=O)C1(F)C#CCCCCC1)ON1C(=O)CCC1=O]

16. The method of any one of embodiments 12 to 14, wherein the compound having the formula $X_1$-L-$X_2$ is:

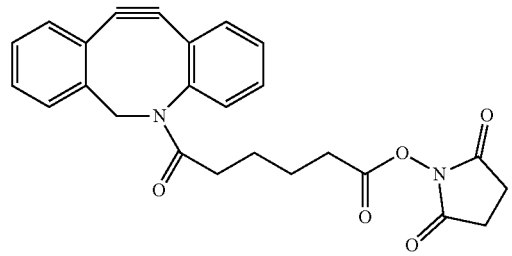 [SMILES: O=C(CCCCC(=O)N1Cc2ccccc2C#Cc2ccccc21)ON1C(=O)CCC1=O]

17. The method of any one of embodiments 12 to 14, wherein the compound having the formula $X_1$-L-$X_2$ is:

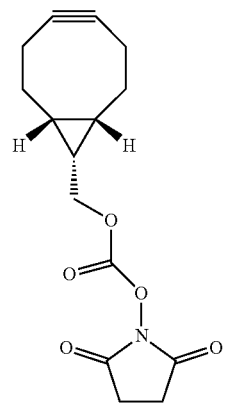 [SMILES: O=C(OC[C@@H]1[C@@H]2CCC#CCC[C@@H]21)ON1C(=O)CCC1=O]

18. A saccharide derivative comprising an eight-membered cycloalkyne group.

19. The saccharide derivative of embodiment 18, wherein the eight-membered cycloalkyne group is a cyclooctyne group.

20. The saccharide derivative according to embodiment 18, obtainable by the method of any one of embodiments 1 to 17.

21. A method of conjugating a saccharide derivative as defined in any one of embodiments 18 to 20 to an azide-containing moiety, comprising reacting the eight-membered cycloalkyne group with the azide to form a triazole linkage.

22. The method of embodiment 21, wherein the saccharide derivative is produced according to the method of any one of embodiments 1 to 17.

23. The method of embodiment 21 or embodiment 22, wherein the method is carried out in the absence of a metal catalyst.

24. The method of any one of embodiments 21 to 23, wherein the conjugation occurs via a [3+2] cycloaddition reaction.

25. The method of any one of embodiments 21 to 25, wherein the azide-containing moiety is a carrier molecule.

26. The method of embodiment 25, wherein the carrier molecule is a protein.

27. The method of embodiment 26, wherein the protein is a GBS protein.

28. The method of embodiment 27, wherein the GBS protein is GBS67 or GBS80.

29. The method of any one of embodiments 21 to 28, wherein the azide-containing moiety includes a spacer.

30. The method of embodiment 29, wherein the azide-containing moiety is a carrier protein containing at least one derivatized tyrosine residue having the following structure, wherein the azide is attached via the 3H-1,2,4-triazole-3,5(4H)-dione:

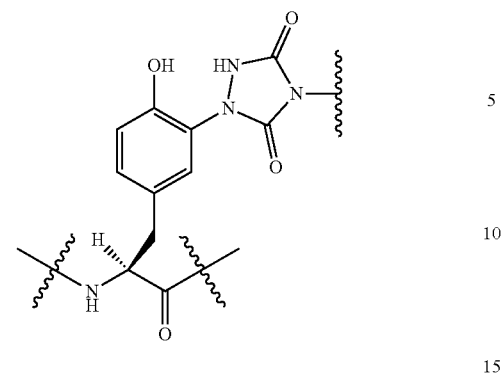

31. The method of any one of embodiments 21 to 30, wherein the azide is present as a terminal group in the azide-containing moiety.

32. The method of embodiment 31, wherein the azide-containing moiety is a carrier protein containing at least one derivatized tyrosine residue having the following structure:

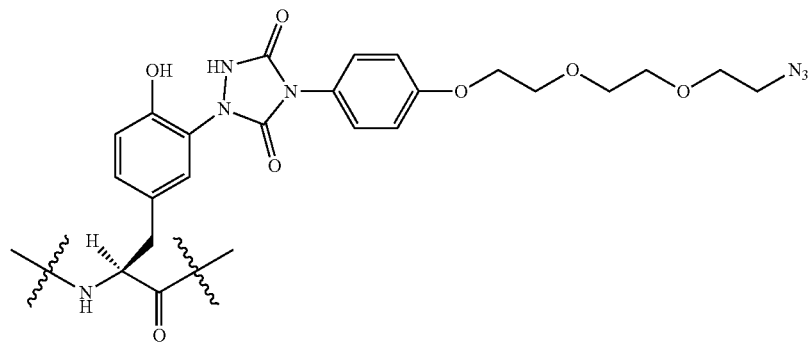 [SMILES: *N[C@@H](Cc1ccc(O)c(-n2[nH]c(=O)n(-c3ccc(OCCOCCOCCN=[N+]=[N-])cc3)c2=O)c1)C(*)=O]

33. A conjugate of a saccharide derivative as defined in any one of embodiments 18 to 20 and an azide-containing moiety, wherein the conjugate has the formula R-S-T, wherein R comprises a residue of the saccharide derivative, S is a triazole group fused to an eight-membered cycloalkyl group and T comprises a residue of the azide-containing moiety.

34. The conjugate of embodiment 33, wherein the conjugate includes a spacer in the residue of the saccharide derivative between the saccharide and S.

35. The conjugate of embodiment 34, wherein the spacer has the formula —NH—C(O)—(CH$_2$)$_n$—NH—C(O)—, where n is 1, 2, 3, 4, 5, 6, 7, 8, 9 or 10.

36. The conjugate of embodiment 35, wherein n is 5.

37. The conjugate of any one of embodiments 33 to 36, wherein the conjugate includes a spacer in the residue of the azide-containing moiety between the moiety and S.

38. The conjugate of embodiment 37, wherein the spacer has the formula —[(CH$_2$)$_2$O]$_n$—, where n is 1, 2, 3, 4, 5, 6, 7, 8, 9 or 10.

39. The conjugate of embodiment 38, wherein n is 3.

40. The conjugate of any one of embodiments 33 to 39, wherein the conjugate includes a spacer in the residue of the saccharide derivative between the saccharide and S and a spacer in the residue of the azide-containing moiety between the moiety and S.

41. The conjugate of any one of embodiments 33 to 40, wherein R-S-T is:

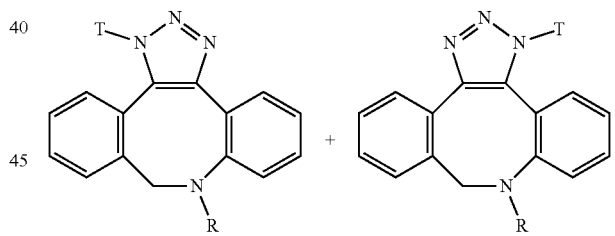

42. The conjugate of any one of embodiments 33 to 40, wherein R-S-T is:

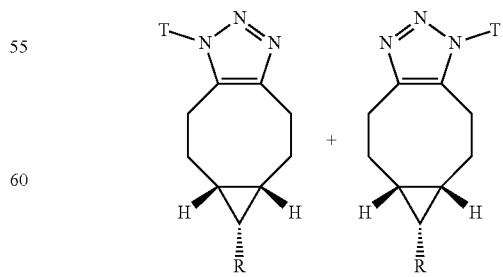

43. The conjugate of any one of embodiments 33 to 40, wherein R-S-T is:

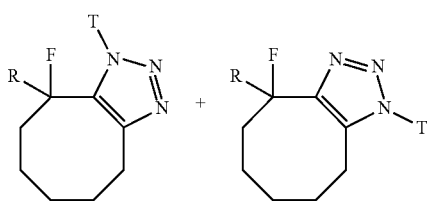

44. The conjugate of any one of embodiments 33 to 43, obtainable by the method of any one of embodiments 21 to 32.

45. A pharmaceutical composition comprising a conjugate of the invention in combination with a pharmaceutically acceptable carrier.

46. A method for raising an immune response in a mammal, comprising administering a 10 conjugate or pharmaceutical composition according to any one of embodiments 33 to 43 to the mammal.

REFERENCES

[1] *Peptide Science* (2010), 94 (1), 95.
[2] Kolb et al., (2004) *Angew Chem Int Ed* 40, 3004
[3] Evans (2007) *Aust J Chem* 60, 384.
[4] Tornoe et al. (2002) *J Organic Chem* 67, 3057
[5] Rostovstev et al., (2002) *Angew Chem Int Ed* 41, 2596
[6] Agard et al., (2004) *J Am Chem Soc* 126, 15046
[7] *Pure Appl. Chem.* (1984), 56, 893.
[8] *Nature Reviews* (2006) 4, 509.
[9] WO2006/050341
[10] Guttormsen et al. (2008) Proc Natl Acad Sci USA. 105 (15): 5903-8. Epub 2008 Mar. 31.
[11] WO96/40795
[12] Michon et al. (2006) Clin Vaccine Immunol. 2006 August; 13 (8): 936-43.
[13] Lewis et al. (2004) *PNAS USA* 101:11123-8.
[14] Wessels et al. (1989) *Infect Immun* 57:1089-94.
[15] WO2006/082527.
[16] WO2009/081276.
[17] Ravenscroft et al. (1999) *Vaccine* 17:2802-2816.
[18] Costantino et al. (1999) *Vaccine* 17:1251-1263.
[20] WO02/058737.
[20] Frash (1990) p.123-145 of *Advances in Biotechnological Processes* vol. 13 (eds. Mizrahi & Van Wezel)
[21] WO03/007985.
[22] Inzana (1987) *Infect. Immun.* 55:1573-1579.
[23] WO200/5103230
[24] Kandil et al. (1997) *Glycoconj J* 14:13-17.
[25] Berkin et al. (2002) *Chemistry* 8:4424-4433.
[26] Glode et al. (1979) *J Infect Dis* 139:52-56
[27] WO94/05325; U.S. Pat. No. 5,425,946.
[28] WO2005/033148.
[29] WO03/080678.
[30] WO2008/084411
[31] Nilsson & Svensson (1979) *Carbohydrate Research* 69:292-296)
[32] Tokunaka et al. (1999) *Carbohydr Res* 316:161-172.
[33] WO03/097091
[34] Pang et al. (2005) *Biosci Biotechnol Biochem* 69:553-8.
[35] Read et al. (1996) *Carbohydr Res.* 281:187-201.
[36] Takeo and Tei (1986) *Carbohydr Res.* 145:293-306
[37] Tanaka et al. (2003) *Tetrahedron Letters* 44:3053-3057
[38] Ning et al. (2002) *Tetrahedron Letters* 43:5545-5549
[39] Geurtsen et al. (1999) *Journal of Organic Chemistry* 64 (21): 7828-7835
[40] Wu et al. (2003) *Carbohydr Res.* 338:2203-12
[41] Nicolaou et al. (1997) *J. Am. Chem. Soc.* 119:449-450
[42] Yamada et al. (1999) *Tetrahedron Letters* 40:4581-4584
[43] Yamago et al. (2001) *Org. Lett.* 24:3867-3870
[44] Yuguo et al. (2004) *Tetrahedron* 60:6345-6351
[45] Amaya et al. (2001) *Tetrahedron Letters* 42:9191-9194
[46] Mei et al. (2005) *Carbohydr Res.* 340:2345-2351
[47] Takeo et al. (1993) *Carbohydr Res.* 245:81-96
[48] Jamois et al. (2005) *Glycobiology* 15 (4): 393-407
[49] Lefeber et al. (2001) *Chem. Eur. J.* 7 (20): 4411-4421
[50] Huang et al. (2005) *Carbohydr Res.* 340:603-608
[51] U.S. Pat. No. 5,508,191.
[52] MiKyoung et al. (2003) *Biochemical Engineering Journal*, 16:163-8.
[53] Barsanti et al. (2001) *J Appl Phycol* 13:59-65.
[54] Bardotti et al. (2008) *Vaccine* 26:2284-96
[55] Jones (2005) *An. Acad. Bras. Cienc,* 77 (2) 293-324.
[56] Jones (2005) *J Pharm Biomed Anal* 38 840-850.
[57] Moreau et al. (1990) *Carbohydrate Res.* 339 (5): 285-91
[58] Fournier et al. (1984) *Infect. Immun.* 45 (1): 87-93.
[59] Jones (2005) *Carbohydrate Res.* 340 (6): 1097-106.
[60] Fattom et al. (1998) *Infect Immun.* 66 (10): 4588-92
[61] Lemercinier and Jones (1996) *Carbohydrate Res.* 296: 83-96.
[62] Jones and Lemercinier (2002) *J Pharm Biomed Anal.* 30 (4): 1233-47.
[63] WO05/033148
[64] WO 00/56357
[65] Hestrin (1949) *J. Biol. Chem.* 180:249-261.
[66] Konadu et al. (1994) *Infect. Immun.* 62:5048-5054.
[67] Fattom et al. (1990) *Infect Immun.* 58 (7): 2367-74
[68] Gilbert et al. (1994) *J. Microb. Meth.* 20:39-46.
[69] Kreis et al. (1995) *Int J Biol Macromol.* 17 (3-4): 117-30.
[70] Höög et al. (2002) *Carbohydr Res.* 337 (21-23): 2023-36
[71] www.polymer.de
[72] U.S. Pat. No. 4,356,170.
[73] U.S. Pat. Nos. 4,356,170 and 4,663,160
[74] U.S. Pat. No. 4,711,779.
[75] WO00/10599.
[76] U.S. Pat. No. 4,057,685.
[77] WO2012/075361.
[78] Wan et al. (2006) *J Org Chem,* 71, 8244
[79] WO2005/000346
[80] Anonymous (January 2002) *Research Disclosure,* 453077.
[81] Anderson (1983) *Infect Immun* 39 (1): 233-238.
[82] Anderson et al. (1985) *J Clin Invest* 76 (1): 52-59.
[83] EP-A-0372501.
[84] EP-A-0378881.
[85] EP-A-0427347.
[86] WO93/17712
[87] WO94/03208.
[88] WO98/58668.
[89] EP-A-0471177.
[90] WO91/01146
[91] Falugi et al. (2001) *Eur J Immunol* 31:3816-24.
[92] Baraldo et al. (2004) *Infect Immun* 72:4884-87.
[93] EP-A-0594610.
[94] WO00/56360.
[95] WO02/091998.
[96] Kuo et al. (1995) *Infect Immun* 63:2706-13.
[97] WO01/72337
[98] WO00/61761.
[99] WO00/33882.

[100] WO2004/041157.
[101] WO 2012/035519
[102] WO96/40242.
[103] Lei et al. (2000) *Dev Biol (Basel)* 103:259-264.
[104] WO00/38711
[105] WO99/24578.
[106] WO99/36544.
[107] WO99/57280.
[108] WO00/22430.
[109] Tettelin et al. (2000) *Science*, 287, 1809.
[110] WO96/29412.
[111] Pizza et al. (2000) *Science*, 287, 1816.
[112] WO01/52885.
[113] Bjune et al. (1991) *Lancet*, 338, 1093.
[114] Fukasawa et al. (1999) *Vaccine*, 17, 2951.
[115] Rosenqvist et al. (1998) *Dev. Biol. Stand.*, 92, 323.
[116] Costantino et al. (1992) *Vaccine*, 10, 691.
[117] WO03/007985.
[118] Watson (2000) *Pediatr. Infect. Dis. J.*, 19, 331.
[119] Rubin (2000) *Pediatr. Clin. North. Am.*, 47, 269.
[120] Jedrzejas (2001) *Microbiol. Mol. Biol. Rev.*, 65, 187.
[121] Bell (2000) *Pediatr. Infect. Dis. J.*, 19, 1187.
[122] Iwarson (1995) *APMIS*, 103, 321.
[123] Gerlich et al. (1990) *Vaccine*, 8, S63-68 & 79-80.
[124] Hsu et al. (1999) *Clin. Liver. Dis.*, 3, 901.
[125] Gustafsson et al. (1996) *N. Engl. J. Med.*, 334, 349.
[126] Rappuoli et al. (1991) *TIBTECH*, 9, 232.
[127] *Vaccines* (2004) eds. Plotkin & Orenstein. ISBN 0-7216-9688-0.
[128] WO02/02606.
[129] Kalman et al. (1999) *Nature Genetics* 21:385-389.
[130] Read et al. (2000) *Nucleic Acids Res* 28:1397-406.
[131] Shirai et al. (2000) *J. Infect. Dis.* 181 (Suppl 3): S524-S527.
[132] WO99/27105.
[133] WO00/27994.
[134] WO00/37494.
[135] WO99/28475.
[136] Ross et al. (2001) *Vaccine*, 19, 4135.
[137] Sutter et al. (2000) *Pediatr. Clin. North. Am.*, 47, 287.
[138] Zimmerman & Spann (1999) *Am. Fam. Physician.*, 59, 113-118, 125-126.
[139] Dreesen (1997) *Vaccine*, 15 Suppl, S2.
[140] *MMWR Morb. Mortal. Wkly. Rep.* (1998), 47, 12, 19.
[141] McMichael (2000) *Vaccine*, 19 Suppl 1, S101.
[142] WO02/34771.
[143] Dale (1999) *Infect. Dis. Clin. North. Am.*, 13, 227, viii.
[144] Ferretti et al. (2001) *PNAS USA*, 98, 4658.
[145] WO03/093306.
[146] WO2004/018646.
[147] WO2004/041157.
[148] Ichiman and Yoshida (1981) *J. Appl. Bacteriol.*, 51, 229.
[149] U.S. Pat. No. 4,197,290
[150] Ichiman et al. (1991) *J. Appl. Bacteriol.*, 71, 176.
[151] Robinson & Torres (1997) *Seminars in Immunology*, 9, 271.
[152] Donnelly et al. (1997) *Annu. Rev. Immunol.*, 15, 617.
[153] Scott-Taylor & Dalgleish (2000) *Expert. Opin. Investig. Drugs*, 9, 471.
[154] Apostolopoulos & Plebanski (2000) *Curr. Opin. Mol. Ther.*, 2, 441.
[155] Ilan (1999) *Curr. Opin. Mol. Ther.*, 1, 116.
[156] Dubensky et al. (2000) *Mol. Med.*, 6, 723.
[157] Robinson & Pertmer (2000) *Adv. Virus Res.*, 55, 1.
[158] Donnelly et al. (2000) *Am. J. Respir. Crit. Care Med.*, 162, S190.
[159] Davis (1999) *Mt. Sinai J. Med.*, 66, 84.
[160] Gennaro (2000) *Remington: The Science and Practice of Pharmacy.* 20th edition.
[161] WO03/009869.
[162] Almeida & Alpar (1996) *J. Drug Targeting*, 3, 455.
[163] Agarwal & Mishra (1999) *Indian J. Exp. Biol.*, 37, 6.
[164] WO00/53221.
[165] Jakobsen et al. (2002) *Infect. Immun.*, 70, 1443.
[166] Bergquist et al. (1998) *APMIS*, 106, 800.
[167] Baudner et al. (2002) *Infect. Immun.*, 70, 4785.
[168] Ugozzoli et al. (2002) *J. Infect. Dis.*, 186, 1358.
[169] *Vaccine Design* (1995) Powell & Newman, Plenum.
[170] WO00/23105.
[171] WO90/14837.
[172] Podda (2001) *Vaccine*, 19, 2673.
[173] Frey et al. (2003) *Vaccine*, 21, 4234.
[174] U.S. Pat. No. 6,299,884.
[175] U.S. Pat. No. 6,451,325.
[176] U.S. Pat. No. 5,057,540.
[177] WO96/33739.
[178] EP-A-0109942.
[179] WO96/11711.
[180] WO00/07621.
[181] Barr et al. (1998) *Advanced Drug Delivery Reviews*, 32, 247.
[182] Sjolanderet et al. (1998) *Advanced Drug Delivery Reviews*, 32, 321.
[183] Niikura et al. (2002) *Virology*, 293, 273.
[184] Lenz et al. (2001) *J. Immunol.*, 166, 5346.
[185] Pinto et al. (2003) *J. Infect. Dis.*, 188, 327.
[186] Gerber et al. (2001) *Virol.*, 75, 4752.
[187] WO03/024480.
[188] WO03/024481.
[189] Gluck et al. (2002) *Vaccine*, 20, B10.
[190] EP-A-0689454.
[191] Johnson et al. (1999) *Bioorg. Med. Chem. Lett.*, 9, 2273.
[192] Evans et al. (2003) *Expert Rev. Vaccines*, 2, 219.
[193] Meraldi et al. (2003) *Vaccine*, 21, 2485.
[194] Pajak et al. (2003) *Vaccine*, 21, 836.
[195] Kandimalla et al. (2003) *Nucleic Acids Research*, 31, 2393.
[196] WO02/26757.
[197] WO99/62923.
[198] Krieg (2003) *Nature Medicine*, 9, 831.
[199] McCluskie et al. (2002) *FEMS Immunology and Medical Microbiology*, 32, 179.
[200] WO98/40100.
[201] U.S. Pat. No. 6,207,646.
[202] U.S. Pat. No. 6,239,116.
[203] U.S. Pat. No. 6,429,199.
[204] Kandimalla et al. (2003) *Biochemical Society Transactions*, 31, 654.
[205] Blackwell et al. (2003) *J. Immunol.*, 170, 4061.
[206] Krieg (2002) *Trends Immunol.*, 23, 64.
[207] WO01/95935.
[208] Kandimalla et al. (2003) *BBRC*, 306, 948.
[209] Bhagat et al. (2003) *BBRC*, 300, 853.
[210] WO03/035836.
[211] WO95/17211.
[212] WO98/42375.
[213] Beignon et al. (2002) *Infect. Immun.*, 70, 3012.
[214] Pizza et al. (2001) *Vaccine*, 19, 2534.
[215] Pizza et al. (2000) *Int. J. Med. Microbiol.*, 290, 455.
[216] Scharton-Kersten et al. (2000) *Infect. Immun.*, 68, 5306.
[217] Ryan et al. (1999) *Infect. Immun.*, 67, 6270.

[218] Partidos et al. (1999) *Immunol. Lett.*, 67, 209.
[219] Peppoloni et al. (2003) *Expert. Rev. Vaccines*, 2, 285.
[220] Pine et al. (2002) *J. Control. Release.*, 85, 263.
[221] Domenighini et al. (1995) *Mol. Microbiol.*, 15, 1165.
[222] WO99/40936.
[223] WO99/44636.
[224] Singh et al. (2001) *J. Cont. Release.*, 70, 267.
[225] WO99/27960.
[226] U.S. Pat. No. 6,090,406.
[227] U.S. Pat. No. 5,916,588.
[228] EP-A-0626169.
[229] WO99/52549.
[230] WO01/21207.
[231] WO01/21152.
[232] Andrianov et al. (1998) *Biomaterials*, 19, 109.
[233] Payne et al. (1998) *Adv. Drug Delivery Review*, 31, 185.
[234] Stanley (2002) *Clin. Exp. Dermatol.*, 27, 571.
[235] Jones (2003) *Curr. Opin. Investig. Drugs*, 4, 214.
[236] WO04/60308.
[237] WO04/64759.
[238] WO99/11241.
[239] WO94/00153.
[240] WO98/57659.
[241] European patent applications 0835318, 0735898 and 0761231.
[242] Glezen & Alpers (1999) *Clin. Infect. Dis.* 28:219-224
[243] Madoff et al. (1994) *J Clin Invest* 94:286-92.
[244] Paoletti et al. (1994) *Infect Immun* 62:3236-43.
[245] Gennaro (2000) *Remington: The Science and Practice of Pharmacy*. 20th edition.
[246] Colowick & Kaplan, *Methods In Enzymology*, Academic Press, Inc.
[247] *Handbook of Experimental Immunology*, Vols. I-IV (D. M. Weir and C. C. Blackwell, eds, 1986, Blackwell Scientific Publications).
[248] Sambrook et al. (2001) *Molecular Cloning: A Laboratory Manual*, 3rd edition (Cold Spring Harbor Laboratory Press).
[249] *Handbook of Surface and Colloidal Chemistry* (Birdi, K. S. ed., CRC Press, 1997).
[250] Ausubel et al. (eds) (2002) *Short protocols in molecular biology*, 5th edition (Current Protocols).
[251] *Molecular Biology Techniques: An Intensive Laboratory Course*, (Ream et al., eds., 1998, Academic Press)
[252] *PCR (Introduction to Biotechniques Series)*, 2nd ed. (Newton & Graham eds., 1997, Springer Verlag)
[253] WO2012/035519

The invention claimed is:

1. A method of producing a cycloalkyne-containing saccharide derivative comprising attaching an eight-membered cycloalkyne group to a saccharide, wherein the saccharide is a *Streptococcus agalactiae* (GBS) capsular saccharide from serotype Ia, Ib, II, III or V.

2. A method of producing a cycloalkyne-containing saccharide derivative comprising attaching a group, via a spacer, to a saccharide, wherein the group is selected from:
   (a) an 8 membered cycloalkyne group;
   (b) an 8 membered cycloalkyne is-fused to a cyclopropane group;
   (c) an 8 membered cycloalkyne is-fused to two benzene groups;
   (d) an 8 membered cycloalkyne that is a cyclooctyne group;
   (e) a cyclooctyne group having the structure

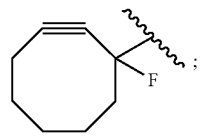

and
wherein the group:
   (i) is attached to the saccharide via the spacer, wherein the group is on a terminus of the spacer; and/or
   (ii) is attached to the saccharide via the spacer, wherein the group is on a terminus of the spacer and wherein the other terminus of the spacer has a functional group for an attachment to the saccharide, and wherein the saccharide is a *Streptococcus agalactiae* (GBS) capsular saccharide from serotype Ia, Ib, II, III or V.

3. The method of claim 2, further comprising:
introducing an aldehyde into the saccharide by oxidizing the saccharide or introducing an amine into the saccharide by oxidizing the saccharide and performing reductive amination on the oxidized saccharide,
wherein the group is attached to the saccharide via the spacer, wherein the group is on a terminus of the spacer and wherein the other terminus of the spacer has a functional group for an attachment to the saccharide, and
wherein the attachment is carried out using a compound having the formula $X_1$-L-$X_2$, wherein $X_1$ is the group and $X_2$-L is the spacer in which $X_2$ is a group that can react with a functional group an amine or aldehyde on the saccharide and L is a linking moiety in the spacer.

4. The method of claim 3, wherein $X_2$ is N-oxysuccinimide.

5. The method of claim 3, wherein L has a formula -$L^3$-$L^2$-$L^1$, wherein $L^1$ is carbonyl, $L^2$ is a straight chain alkyl with 1 to 10 carbon atoms or $L^2$ is absent, and $L^3$ is —NHC(O)—, carbonyl or —O(CH$_3$)—.

6. The method of claim 3, wherein the compound having the formula $X_1$-L-$X_2$ is:

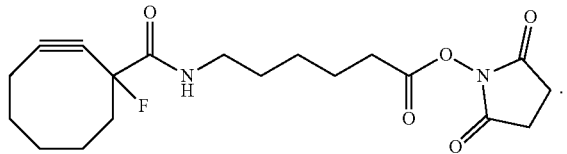 [SMILES: O=C(CCCCCNC(=O)C1(F)C#CCCCCC1)ON1C(=O)CCC1=O]

7. The method of claim 3, wherein the compound having the formula $X_1$-L-$X_2$ is:

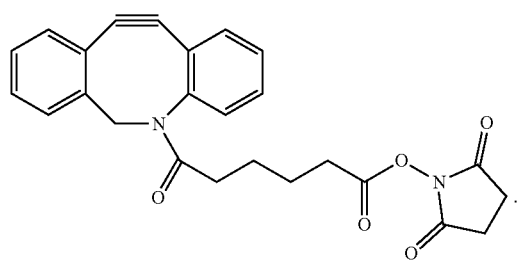 [SMILES: O=C(CCCCC(=O)N1Cc2ccccc2C#Cc2ccccc21)ON1C(=O)CCC1=O]

8. The method of claim 3, wherein the compound having the formula $X_1$-L-$X_2$ is:

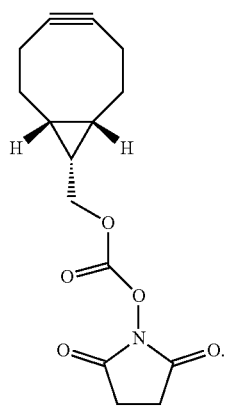 [SMILES: O=C(OC[C@@H]1[C@@H]2CCC#CCC[C@@H]21)ON1C(=O)CCC1=O]

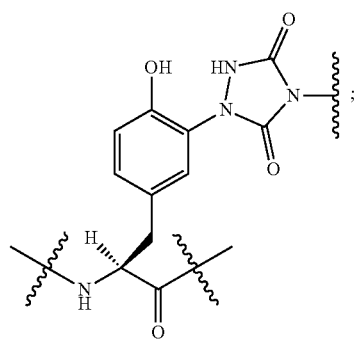 [SMILES: *N[C@@H](Cc1ccc(O)c(-n2[nH]c(=O)n(*)c2=O)c1)C(*)=O]

(e) wherein the azide is present as a terminal group in the azide-containing moiety; and/or (f) wherein the azide is present as a terminal group in the azide-containing moiety, wherein the azide-containing moiety is a carrier protein containing at least one derivatized tyrosine residue having the following structure:

9. A method of conjugating the cycloalkyne-containing saccharide derivative of claim 4, wherein the group is an eight-membered cycloalkyne that is a cyclooctyne group, to an azide-containing moiety, comprising reacting the eight-membered cycloalkyne with the azide to form a triazole linkage, wherein the azide-containing moiety is a protein.

10. The method of claim 9, wherein:
   (a) the method is carried out in the absence of a metal catalyst; or
   (b) the method is carried out in the absence of a metal catalyst, wherein the conjugation occurs via a [3+2] cycloaddition reaction.

11. The method of claim 9, wherein:
   (a) the protein is a GBS protein;
   (b) the protein is GBS67;
   (c) the azide-containing moiety includes a spacer;
   (d) the azide-containing moiety includes a spacer and wherein the azide-containing moiety is a carrier protein containing at least one derivatized tyrosine residue having the following structure, wherein the azide is attached via the 3H-1,2,4-triazole-3,5 (4H)-dione:

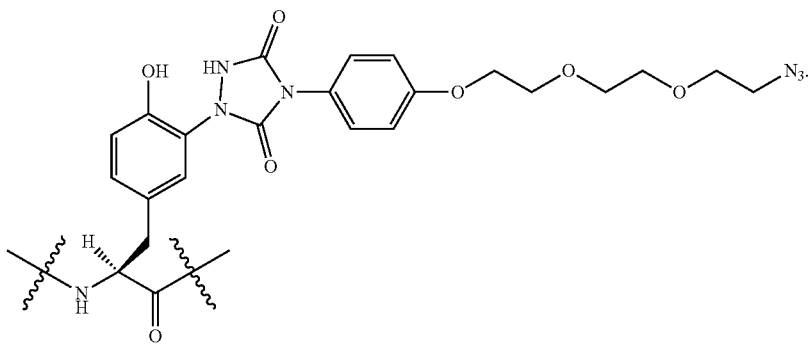 [SMILES: *N[C@@H](Cc1ccc(O)c(-n2[nH]c(=O)n(-c3ccc(OCCOCCOCCN=[N+]=[N-])cc3)c2=O)c1)C(*)=O]

12. The method of claim 2, wherein the eight-membered cyclooctyne group is

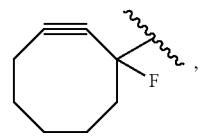 [SMILES: *C1(F)C#CCCCCC1]

wherein the eight-membered cyclooctyne group and the saccharide are covalently linked via a spacer having a formula —NH—C(O)—(CH$_2$)$_n$—NH—C(O)—, where n is 1, 2, 3, 4, 5, 6, 7, 8, 9, or 10; and wherein the terminal —NH— is attached to a carbon atom of the saccharide and the terminal —C(O)— is attached to the eight-membered cyclooctyne group.

13. The method of claim 1, wherein the saccharide is a *Streptococcus agalactiae* (GBS) capsular saccharide from the serotype II or V.

* * * * *